US006196156B1

(12) United States Patent
Denesuk et al.

(10) Patent No.: US 6,196,156 B1
(45) Date of Patent: *Mar. 6, 2001

(54) BEDDING ARTICLES POSSESSING MICROBE-INHIBITING PROPERTIES

(75) Inventors: Matthew Denesuk; Eugenie V. Uhlmann, both of Tucson, AZ (US); Maryclay Smith; Erin Hingst, both of Powhatan, VA (US)

(73) Assignee: Seefar Technologies, Inc., Tucson, AZ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/059,893

(22) Filed: Apr. 14, 1998

Related U.S. Application Data

(60) Provisional application No. 60/043,014, filed on Apr. 15, 1997.

(51) Int. Cl.$^7$ ............................. A01K 29/00; A47C 20/02
(52) U.S. Cl. ............................ 119/28.5; 5/690; 5/698; 5/636
(58) Field of Search .................... 119/28.5, 169, 119/526, 652; 5/690, 636, 653, 652, 698

(56) References Cited

U.S. PATENT DOCUMENTS

| | | | | |
|---|---|---|---|---|
| 3,638,255 | * | 2/1972 | Sterrett ............................ | 5/641 |
| 3,902,456 | * | 9/1975 | David ............................. | 119/28.5 |
| 3,965,503 | * | 6/1976 | Gridel ............................ | 5/334 R |
| 3,968,530 | * | 7/1976 | Dyson ............................ | 5/676 |
| 4,517,919 | * | 5/1985 | Benjamin et al. . | |
| 4,525,409 | * | 6/1985 | Elesh ............................ | 428/193 |
| 4,525,410 | * | 6/1985 | Hagiwara et al. ................. | 428/198 |
| 4,801,493 | * | 1/1989 | Ferziger et al. .................. | 442/123 |
| 5,038,431 | * | 8/1991 | Burgin et al. .................... | 5/641 |

(List continued on next page.)

FOREIGN PATENT DOCUMENTS

| | | | |
|---|---|---|---|
| 1384775 | * | 2/1975 | (GB) . |
| 2248774 | * | 4/1992 | (GB) . |

OTHER PUBLICATIONS

Affidavit of Dennis Curley of Lazy Pet, Dated May 29, 1997, 2 Pages.
*Ultra–Fresh* Antimicrobials Brochure Undated, 1 Page.
Typical *Ultra–Fresh* * Uses Brochure Undated, 1 Page.
Examples of Micro–Organisms That *Ultra–Fresh* * Products Inhibit Brochure Undated, 1 Page.

(List continued on next page.)

*Primary Examiner*—Michael J. Carone
*Assistant Examiner*—James S. Bergin
(74) *Attorney, Agent, or Firm*—Rader, Fishman, Grauer & Mc Garry

(57) ABSTRACT

A bedding article for a domestic animal comprising an outer textile casing defining a geometric shape for supporting a domestic animal, an inner filling, and a microbe-inhibiting agent or property applied to at least one of the outer textile casing and the inner filling. The bedding article may be fabricated in various shapes, designs, and styles; e.g., rectangular, circular, elliptical, with or without upstanding side walls, etc. A process for applying the microbe-inhibiting agent or property to at least one on the outer textile casing and the inner filling is provided. Application methods include spraying, dipping, brushing, and rolling the microbe-inhibiting agent or property onto at least one of the outer textile casing and the inner filling. An alternative embodiment includes an outer textile casing defining a geometric shape for supporting a domestic animal, an inner filling, a lining therebetween, and a microbe-inhibiting agent or property applied to at least one of the outer textile casing, the inner lining, and the inner filling.

57 Claims, 4 Drawing Sheets

U.S. PATENT DOCUMENTS

| | | | |
|---|---|---|---|
| 5,233,787 | * 8/1993 | Andersen | 43/132.1 |
| 5,299,335 | * 4/1994 | Ivester et al. | 5/641 |
| 5,350,625 | * 9/1994 | Peterson et al. | 428/219 |
| 5,509,373 | * 4/1996 | Elesh | 119/28.5 |
| 5,515,811 | * 5/1996 | McAlister | 119/28.5 |
| 5,653,195 | * 8/1997 | Young | 119/526 |
| 5,724,911 | * 3/1998 | McAlister | 119/28.5 |
| 5,928,755 | * 7/1999 | Mullen | 428/102 |
| 5,970,919 | * 10/1999 | Mooney | 119/526 |

OTHER PUBLICATIONS

Examples of Antimicrobial Testing (*Ultra–Fresh*) Brochure Undated, 1 Page.

A Sample of Microbial Test Methods Available Brochure Undated, 1 Page.

Letter from Ron Tatar of Crain Industries, Inc. to Dennis Curley re: Anti–Microbial additive suppliers Undated, 1 Page.

Letter from Ron Tatar of Crain Industries, Inc. to Dennis Curley re: Anti–Microbial Additives for Polyurethane Foam Undated. 1 Page.

Technical Data Sheet, *Ultra–Fresh*®DM–50 from Thomson Research Associates Undated, 4 Pages.

Antimicrobial Activity on Garments Undated, 2 Pages.

Milliguard, Retards the Growth of the Following Micro–Organisms, Undated, 2 Pages.

Fortrel Bactishield, The Antimicrobial Fiber Brochure Undated, 2 Pages.

Letter from C. Kel Little of Precison Fabrics Group, Inc. to Luis Didonato, Subject: Antimicrobial Undated, 1 Page.

Aegis® High Density Brochure Undated, 1 Page.

Effects of Microbial Growth in the Skin, Uniform Fabric Environment Undated, 2 Pages.

A New, Durable Antimicrobial Finish for Textiles* Richard L. Gettings, Dow Corning Corp., and Benny L. Triplett, Burlington Industries, Undated, 4 Pages.

Letter from Mike Sanders, Vice Pres. of Cal–Pacific Dyeing & Finishing Corp., to Luis Didonato of Lazy Pet, and attached speck sheet on the Durable Bacteriostatic and Fungistatic agent Undated, 2 Pages.

Vinyzene® Antimicrobial Additives for Plastics, Product Information Mortan Plastics Additives, Undated, 2 Pages.

Vinyzene® Material Safety Data Sheet Morton International, Inc., Dec. 18, 1996, 6 Pages.

Choose the Right Biocide to Meet Your Needs, Brochure on Cunilate® Morton Plastics Additives, Undated, 5 Pages.

Bio–Pruf™ Treated Brochure Morton International, Inc. Undated, 8 Pages.

Ultra–Fresh Brochure Undated, 2 Pages.

*Ultra–Fresh*\* Brochure Thomson Research Associates, Undated, 8 Pages.

\* cited by examiner

BEDDING ARTICLES POSSESSING MICROBE-INHIBITING PROPERTIES

CROSS-REFERENCE TO RELATED APPLICATION

This application claims the benefit of provisional patent application Ser. No. 60/043,014 filed Apr. 15, 1997.

FIELD OF THE INVENTION

This invention relates generally to bedding articles, principally for domestic animals, and more particularly to a bedding article having a microbe-inhibiting agent or property that substantially inhibits the proliferation of microbes on, within, or around the bedding article. The term "microbe" refers broadly to classes of bacteria, viruses, germs, mold, mildew, fungi, allergens, and other microorganisms. Articles of the present invention provide comfort and health benefits to both pets and people involved with the use of the articles.

DESCRIPTION OF THE RELATED ART

Bedding-type articles for pets are very popular. Such articles can serve several purposes. They can provide a surface upon which the pet may rest which is more comfortable than typical floors. They can also provide a means for confining the pet to a particular location. Although in some cases some training is required, pets can come to recognize the bedding-type article as the appropriate location for sleeping and resting. In addition, blanket-type products can aid in keeping a pet warm and comfortable.

There are great varieties of bedding-type articles available, but no pet bedding articles have been disclosed which possess microbe-inhibiting activity. Bedding-type articles are available, however, which have been treated to repel insects. U.S. Pat. No. 4,008,688 granted to Nicholas and U.S. Pat. No. 1,569,710 granted to Burt disclose the impregnation or saturation of a pet cushion with insecticides. U.S. Pat. No. 3,902,456 granted to David alternatively uses an adhesive in conjunction with an intermediate cushion layer to trap insects.

The proliferation of microbes is often encouraged by a damp environment. Because it is common for pets, especially dogs, to urinate or defecate upon, to salivate upon, deposit partially digested food upon, or otherwise soil their bedding articles; and because such articles are generally porous and absorbent, microbial proliferation is especially problematic. The fact that the articles often remain at favorable incubation temperatures (e.g., partially covered by a dog's body the dog is resting or sleeping) aggravates the problem. These conditions can also make the articles attractive to other pests such as fleas and ticks. Pets using such articles, as well as their owners, may thus be exposed to a significant health hazard. The environment to which such articles are exposed is unique; and the difficulty in designing and developing a product which is efficacious, safe and non-toxic, and is economical to produce, is not easy. This may account for the fact that no one has ever produced microbe-inhibiting bedding articles for pets.

The exteriors of bedding articles for pets may be washed, but it is difficult for typical washing processes to be effective inside the filling of such an article (typically comprised of fiber, foam, beads, etc.). This is due to the difficulty of diffusing the cleaning agents into and out from the materials which comprise the article. Organic and inorganic nutrients for microbes, as well as microbes themselves, often remain after washing.

Bedding articles for pets are typically expensive, and pet owners intend to keep the bedding articles through multiple washings. The microbe-inhibiting qualities must therefore be stable enough to retain their efficacy even after multiple aggressive washings.

Accordingly, there is a real need in the pet products industry for pet bedding articles which are microbe-inhibiting in nature, promote good hygiene, are economical to manufacture, and are at the same time usable in their usual manner by the pets.

SUMMARY OF THE INVENTION

According to the invention, bedding articles for pets have an effective amount of a microbe-inhibiting agent or property which is effective in limiting microbial proliferation, and at the same time is not present in quantity, concentration or nature whereby they may be harmful to the pets or humans who come into contact with the articles. The effective amount of the microbe-inhibiting agent or property limits the spread of the microbe-inhibiting chemicals or agents within and about the article, takes into consideration the patterns of use and material structure of the article.

According to the invention, a textile-based bedding article for a domestic animal comprises an outer textile casing defining a shape in the form of an article of a size which can support a domestic animal, an inner filling and at least one of the outer textile casing and the inner filling having an effective micro-inhibiting agent or property. The outer textile casing can comprise a woven, a non-woven or a knit fabric made from natural or synthetic fibers.

The inner filling for the article can comprise a number of different materials, including, a foam, a particulate material or a fibrous filling. The fibrous filling can be selected from the group consisting of polyolefins, acrylics, nylon, polyester, polyurethane, polyethylene terephthalate, cellulous acetate, triacetate resin fibers and blends thereof. In one embodiment, the microbe-inhibiting agent or property is applied to at least a portion of the fiber in a fibrous filling for the article.

The microbe-inhibiting agent or property can be at least one of a microbe-cidal, microbe-starving and microbe-impenetrable agents. In one embodiment, a microbe-inhibiting agent in the form of a compound can be present in an effective amount depending on the nature of the product, but generally in the range of 0.5 to 10 percent by weight of the article. In another embodiment, the microbe-inhibiting agent is a compound selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, polysubstituted imine salts and phosphate esters, and mixtures thereof. Preferred compounds are chlorine dioxide, 2,4,4'-trichloro-2'-hydroxydiphenyl and the latter is incorporated into at least a portion of resin fibers which constitute the filling or the casing.

In a preferred embodiment the filling comprises acrylic fibers and the 2,4,4'-trichloro-2'-hydroxydiphenyl compound is incorporated into at least some of the acrylic fibers. In another embodiment, the microbe-inhibiting agent or property is applied to the fibers which form either the outer casing or the filling for the article. In another embodiment, the microbe-inhibiting agent or property is bonded to at least a portion of the fibers. In a preferred embodiment of the invention, the microbe-inhibiting agent or property exhibits a zone of influence which extends beyond the portion of the fibers on which the microbe-inhibiting agent or property is incorporated.

The microbe-inhibiting agent or property can be applied to the outer casing. In one embodiment, the outer casing of the article comprises a tightly-woven fabric which prevents the passage of microbes therethrough. In another embodiment, the outer casing comprises a laminate, the inner layer of which has microbe-inhibiting or microbe-cidal properties.

The article according to the invention can have odor-controlling agents in the form of an odor-masking, odor-modifying and an odor-absorbing agent. The article can further include noise-making articles and the article can be washable. Further, at least one of the outer casing and inner filling can be impregnated with a flame-resistant modacrylic polymer.

According to one embodiment of the invention, the amount of microbe-inhibiting agent which is added to the article is computed in accordance with the following formula:

$$C_B = C_{MI} f_{MI}$$

wherein $C_B$ is the concentration of the microbe-inhibiting agent in the entire blend if the agent were to diffuse and become completely homogeneous throughout the blend, $C_{MI}$ is the average concentration of the microbe-inhibiting agent within the initially microbe-inhibiting fiber and $f_{MI}$ is the fraction of the filter blend that is composed of initially microbe-inhibiting fibers.

Further according to the invention, there is provided a method for inhibiting the growth and presence of microbes on a bedding article which can be carried by a domestic animal wherein the bedding article has an outer textile casing defining the shape of the form of the article and an inner filling, the method comprising the step of providing at least one of the outer textile casing and the inner filling with an effective microbe-inhibiting agent or property. The microbe-inhibiting agent or property can be applied to the outer casing or to the inner filling. The outer casing can be a woven, non-woven or knit fabric and the microbe-inhibiting agent or property is in the form of an anti-microbial agent which is applied to the casing or incorporated into the fibrous content of the textile fabric. Alternatively, the microbe-inhibiting agent or property can be a tightly-woven fabric for the casing which impedes the passage of microbes therethrough. Further, the micro-inhibiting agent or property can be a compound which is incorporated into a fibrous filling or applied to a portion of the fibrous filling.

In yet another embodiment of the invention, the outer casing can comprise a laminate of an outer textile fabric and an inner backing layer and the microbe-inhibiting agent or property can comprise a microbe-inhibiting or microbe-cidal property inner layer of the outer casing.

Microbe-inhibiting articles offer many advantages over the bedding articles of the prior art. One advantage is that microbe-inhibiting articles inhibit the growth and proliferation of microbes; and, because microbial growth can create an environment that is attractive for many pests, such articles will inhibit the proliferation of pests as well.

The present invention can, therefore, provide a healthier environment for the pets and their "families" and, in turn, diminish the potential for illnesses, allergic reactions, and general discomfort. The microbe-inhibiting nature of the articles can also inhibit the emission of odors. This, in conjunction with the optional incorporation of an independent anti-odor activity into the articles, can allow the articles to possess a pleasant or neutral scent.

The useful life of articles made in accordance with the invention is prolonged for at least two reasons. First, because the articles will be cleaner and safer, one can comfortably use them for longer periods of time. Second, because microbes and pests can contribute strongly to the physical and chemical degradation of many materials, the textile-based bedding articles according to the invention can possess inherently longer useful lifetimes.

In addition to being safer, having a more pleasant scent, and possessing longer useful lifetimes, the articles of the present invention are more convenient because they require fewer washings than articles of the prior art.

DETAILED DESCRIPTION OF THE INVENTION

Figure 1:
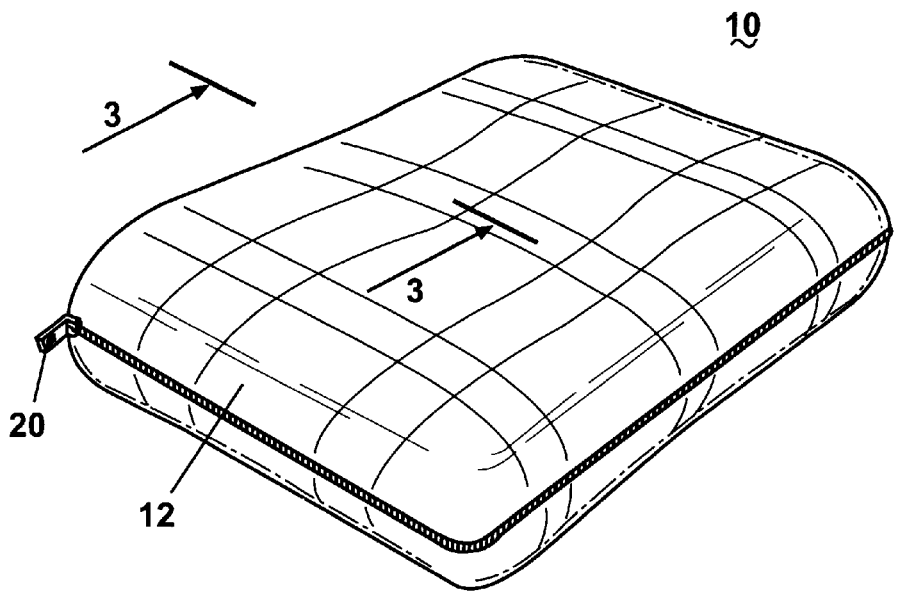
FIG. 1 is a perspective view of a first embodiment of a bedding article for a pet according to the invention.

Referring now to the drawings and to FIG. 1 in particular, first embodiment of a bedding article 10 is shown as having a generally rectangular geometry. While the bedding article 10 has been shown, for illustrative purposes only, as substantially rectangular, any one of a number of peripheral geometries are likewise contemplated for use including the alternative embodiment shown in FIG. 2, which bedding article 110 includes a generally circular base 114 with an upstanding circumferential side wall 112. The only limitation with regard to the peripheral geometry of the bedding article 10, 110 is that it must be configured such that an ordinary domestic animal can recline within or upon the article.

The term "microbe-inhibiting" in the present disclosure subsumes all characteristics (and the means for imparting these characteristics) that causes a pet bedding article to be inhospitable to microbes. In the invention, distinctions are made between three types of microbe inhibition: 1) microbe-cidal, 2) microbe-starving, and 3) microbe-impenetrable.

Microbe-cidal refers to a property whereby microbes are actively killed or otherwise rendered ineffective. If a microbe comes within a sufficiently close range (direct contact, for some materials; within a "zone of inhibition" for others) of a microbe-cidal material, it will be killed or otherwise rendered ineffective. Microbe-cidal properties can be imparted to materials by a variety of means. A preferred means uses microbe-cidal agents during the manufacturing process of the materials and/or treats the materials with microbe-cidal agents. A number of preferred agents are disclosed below. For the microbe-cidal property to be durable, it is often preferred that the agents be bonded in some manner to the materials comprising the bedding article. Such materials exhibit smaller zones of inhibition than materials containing non- or weakly-bonded agents, but the microbe-cidal property with regard to microbes coming directly into contact with the material can be more durable. Using agents which are insoluble or only sparingly soluble in water can also be a key element for durability. As will be seen below, the present invention includes novel considerations involving the bonding of the microbe-cidal agents and their relations to the designs of the bedding article.

Microbe-starving refers to a property whereby microbes are controlled or eliminated by deprivation of sources of nutrition. A material is said to possess microbe-starving properties if microbes in contact with the material have difficulty acquiring the resources they need to survive. One can often provide or enhance a microbe-starving characteristic to a material by changing or altogether eliminating additives to the materials (e.g., plasticizers, fillers, or processing aids). Because adhered dust or liquids can provide nutrition for microbes, it is preferred that the material be provided with anti-adhesion properties (e.g., anti-static, low surface energy, etc.).

Microbe-impenetrable refers to the property of a material or coating whereby a microbe cannot pass through the material or coating. In this case, microbes may proliferate to some degree on a surface of the material, but such proliferation will be confined to the surface. Thus if an article is treated on its exterior by a microbe-impenetrable coating, microbes from the environment will not be able to pass into the interior of the article, will be limited in the degree to which they can proliferate, and can more readily be removed by washing. Appropriate placement of microbe-impenetrable materials is important to their effectiveness in providing the microbe-inhibiting property.

It is often prudent to fight the battle against microbial proliferation on several fronts. Thus, preferred microbe-inhibiting bedding articles will often possess combinations of microbe-inhibiting behavior. For example, when a particular component of a pet bedding article is most susceptible to microbial attack, this component can be treated with both a microbe-impenetrable layer and a microbe-cidal agent, while the remainder of the article is treated with only the microbe-cidal agent. Further, an additive that serves as a resource for microbial growth may be important only for certain parts of the article. For example, plasticizers often act as an effective resource for microbial proliferation; and one can use the plasticizer only where the flexibility is needed, and then treat this area with an effective combination of microbe-inhibiting characteristics; and the remainder of the article, where the plasticizer was not used, may be less vigorously protected.

Physical cleaning can contribute to inhibiting the proliferation of microbes. Organic and inorganic material can act as a barrier between a microbe-inhibiting agent and the unwanted microbes (see, e.g., "The Practical Application of Disinfection and Sterilization in Health Care Facilities," by J. C. Cokendolpher and J. F. Haukos, American Hospital Association, Chicago, Ill., 1996). The microbe-inhibiting properties will therefore frequently be more potent if the article is clean. In addition, many organic materials can provide resources for unwanted microbes. Articles that possess microbe-inhibiting properties and are washable are therefore generally preferred; and articles which are less likely to accumulate organic or inorganic material, due to their structural design or to the materials used, are also preferred.

For durability, the microbe-inhibiting agents should be insoluble or sparingly soluble in the fluids with which they come into contact. This includes fluids associated with their use (saliva, urine, or other bodily fluids) as well as washing and cleaning fluids (the microbe-inhibiting activity should be durable to repeated home laundering). The insolubility may be an intrinsic characteristic of the agent-fluid combination, or it may be due to the fact that the agents are strongly bonded to the materials comprising the article. Both types are included in the present invention.

Although both water-durable and non-water-durable microbe-inhibiting components can be used with effectiveness in the present invention, if a non-water-durable microbe-inhibiting component is used, the exterior of the exposed material should desirably be provided with water-repellent or otherwise water-insulating qualities.

In a preferred class of embodiments, microbe-inhibiting properties are conferred upon one or more of the materials comprising the bedding article by treating the material with or otherwise incorporating into the material a microbe-inhibiting agent. This microbe-inhibiting agent is a chemical species or particle which imparts to the material an effective microbe-inhibiting property. The microbe-inhibiting agents will often function primarily through a microbe-cidal mechanism. The microbe-inhibiting agents are typically chemicals, polymers, solutions (solid or liquid), or particulates (which may possess their own microbe-inhibiting activity or may act as hosts for other microbe-inhibiting agents). These microbe-inhibiting agents can exist in a variety of forms and be held in a variety of hosts before being incorporated into the bedding article. For example, they can be dissolved in a liquid; they can be incorporated in or comprise the totality of a particulate phase, either dry or suspended in a liquid; they can be included within a plasticizer compound; or they can be pre-incorporated into a material used in manufacturing the article (e.g., one can employ materials which already possess microbe-inhibiting properties).

A good review of chemical microbe-inhibiting agents for use in polymers can be found in *Plastics Additives and Modifiers Handbook*, pp. 338–350, J. Edenbaum, Ed., Chapman and Hall, Great Britain, 1996.

The microbe-inhibiting treatment can be carried out at different points during the process of manufacturing the article or its component materials. For example, one can incorporate microbe-inhibiting agents in the fibers as they are being manufactured, which microbe-inhibiting fibers can be used as the filling of stuffed bedding articles or as the fabric used as the external covers of stuffed bedding articles. One can also manufacture a microbe-inhibiting rubber-like material for use in a component of the bedding article that is comprised of (e.g., molded) plastic. One can also treat (as by spraying or dipping) some or all of the materials after they are partially or completely manufactured (e.g., one can treat the external cover and/or the filling or some component of the filling of a stuffed bedding article before its final assembly). Alternatively or in addition, one can treat (as by spraying or dipping) the bedding article when it is finished or nearly finished in its manufacture.

Incorporation of microbe-inhibiting agents into the filler material of a bedding article can be performed in several ways. They can be blended with the filling material such that the agent is dispersed throughout the packed filler (e.g., add a liquid containing the agent to a vat containing the filler material). In this case, depending upon the nature of the filling material, the agent used, and the presence or absence of other compounds (e.g., adhesion promoters, surfactants), the agent can adhere to the filler material and/or the material which confines the filler material; or the agent can remain detached from the filling material or the confining material. The filler material can optionally be treated with chemical agents so that the microbe-inhibiting agents become complexed with all of or part of the filler.

Including the microbe-inhibiting agents within the filler material itself (in intrafiber or intrafoam locations) generally provides greater durability. Intrafiber placement of the agents can be accomplished, inter alia, by known commercial fiber manufacturing techniques.

Some microbe-cidal agents must be in solution to work effectively, while others can be effective in a "raw" state in which they contact directly the microbes. When durability is a dominant concern, the latter are generally preferred; but the former can be used to construct bedding articles in which contact with liquid (as saliva or urine) activates the microbe-cidal properties of the article.

In cases where surface attachment is desired, the use of adhesion promoters is preferred, particularly in conjunction with "raw" microbe-inhibiting agents, i.e., those which do not need to be in solution to work effectively.

When surface attachment to the cover of a bedding article is desired, it is often preferred to use a microbe-cidal/adhesion promoter to bond the microbe-cidal functionality to the cover. It is preferable to bond the agent to both the outer and inner surfaces of the cover; but bonding to only one surface (preferably the outer surface) is often sufficient.

When surface attachment to the filler of a bedding article is desired, it is often preferred to use a microbe-cidal/adhesion promoter to bond the microbe-cidal functionality to the filler.

In cases where a bonding agent is not used to attach the microbe-cidal functionality to the material of interest, or where such bonding is not entirely effective, it is often useful to diminish the rate at which the active microbe-inhibiting agent becomes de-activated. This can be done by inhibiting volatilization or adding stabilizers.

When the microbe-cidal agents are not bonded or are only weakly bonded to materials comprising the bedding article, it is preferred to package the articles such that the effective shelf life of the anti-microbial character is enhanced. For example, when volatilization of the microbe-inhibiting agent or property is a problem, the packaging material can be made impervious to the volatilizing material.

It is useful to have a microbe-inhibiting agent at the surface of the bedding article, as well as in the interior. The microbe-inhibiting agent at the surface can be effective in inhibiting the proliferation of microbes directly on the surface. If suitable microbe-inhibiting agents are present in the interior, they can migrate to the surface as the agent initially at the surface becomes displaced. This process effectively constitutes a "time-release" of microbe-inhibiting agent. In this manner, the concentration of the agent can be maintained at a safe level, any odors associated with unduly high concentrations of the agent are avoided, and the period of effective microbe-inhibiting protection can be considerably prolonged.

The microbe-inhibiting agent can be applied in a liquid form (as dissolved in a solvent) and deposited on the surface of the cover or fiber material. By choosing properly the liquid and material, and optionally any additives, the agent can be made to penetrate the material; and a "time-release" system can be obtained.

A "time-release" property can also be provided by incorporating the active agent in a separate material, optionally particulate, which releases the agent in a time-controlled manner. For example, one can saturate a particulate zeolitic material with a microbe-inhibiting agent and incorporate the zeolitic material into the bedding article. Alternatively, one can use a textile chosen specifically for its time-release characteristics for a particular microbe-inhibiting agent; and this textile can be incorporated in the article. Many other means for providing an effective "time-release" behavior with regard to microbe-inhibiting activity are possible under the present invention. In these cases, the microbe-inhibiting agent will generally function in a microbe-cidal manner.

There are many ways of applying a microbe-inhibiting agent to a piece of material used in a bedding article for a pet. For example, the material can be dipped or passed through a bath of a slurry containing the microbe-inhibiting agent. The material can then be passed through a pair of opposed rollers which control the amount of the slurry mixture retained by the material by controlling the pressure applied to the material as it is passed between the rollers. Upon leaving the squeeze rollers, the material is dried in a process oven. After drying, the material can be further processed by being coiled into rolls and/or cut into the final desired shape and size.

If some form of heat-assisted disinfection of the articles is desired, it is important to use material-agent systems which do not degrade in the disinfection environment (e.g., dishwashers, microwave ovens, conventional ovens, etc.). The softening or decomposition temperatures of the polymers and chemical agents used, for example, must be higher than the disinfection temperature used.

Because the accumulation of undesired organic or inorganic matter may reduce the efficacy of microbe-inhibiting protection, the articles can be designed with materials that reduce the tendency for such accumulation. This result can be accomplished by using low surface energy materials or applying a low surface energy coating; and/or by using anti-static materials or applying an anti-static coating. Non-hydrophilic materials (materials upon which water droplets form contact angles greater than about 30 degrees) are generally preferred to prevent the adhesion of such undesired matter.

It is often preferred to provide some surfaces of the bedding article with both microbe-cidal and anti-adhesion properties. Thus, organic or inorganic matter is less likely to become attached to the article; if such matter does become attached, it is more easily removed; microbes are less likely to attach to or penetrate into the article; and microbes that remain in contact with the surfaces can be eradicated by the microbe-cidal properties of the surfaces. A preferred means of obtaining such a surface is to treat the surface with a combination of a microbe-cidal agent and a low surface energy agent (e.g., a group containing a fluorinated functionality). Both of these agents can be provided with an adhesion promoter functionality as well.

The anti-stick efficiency can be increased by including an anti-static agent, preferably an anti-static agent that can be bonded using an adhesion promoter, as a silane coupling agent.

Pets, especially dogs, often tear or otherwise damage the bedding articles that they use; and they sometimes digest the articles or their components. It is therefore important that the materials are non-toxic and non-carcinogenic at the levels used in the articles. Some agents are non-toxic even at relatively high concentrations (e.g., Triclosan, stabilized chlorine dioxide); other agents are non-toxic at relatively low concentrations, but become toxic at high concentrations (e.g., many unbonded quaternary ammonium compounds). If a bedding article employs a time release property, one must ensure that the time-releasing materials do not contain concentrations of the agents that exceed that can be safely eaten by the animal of interest. Essentially, the pet should be able to eat the article without harm. Also, the treated materials should be non-skin-sensitizing, i.e., should not generally cause allergic or other undesirable reactions on the skin or other membranes of the pet or people who effectively come into contact with the materials.

For safety, durability, microbe-inhibiting efficacy, and ease of use, phenol derivatives, especially 2,4,4'-trichloro-2'-hydroxydiphenol (sometimes known, among other names, as Triclosan, Irgasan, or Microban) incorporated into the constituent materials (e.g., fibers or foam) at the time of manufacture of such materials are particularly preferred. This provides most readily for the microbe-inhibiting agent to become an integral part of the material. These agents in particular can be readily incorporated in the manufacturing processes for the constituent materials; they are generally non-toxic and non-carcinogenic (even at relatively high levels); they generally do not cause adverse skin reactions; they tend to migrate from the bulk of the material to its surface when they are depleted from the surface; and they are very efficacious in inhibiting the proliferation of a wide variety of microbes.

Figure 3:
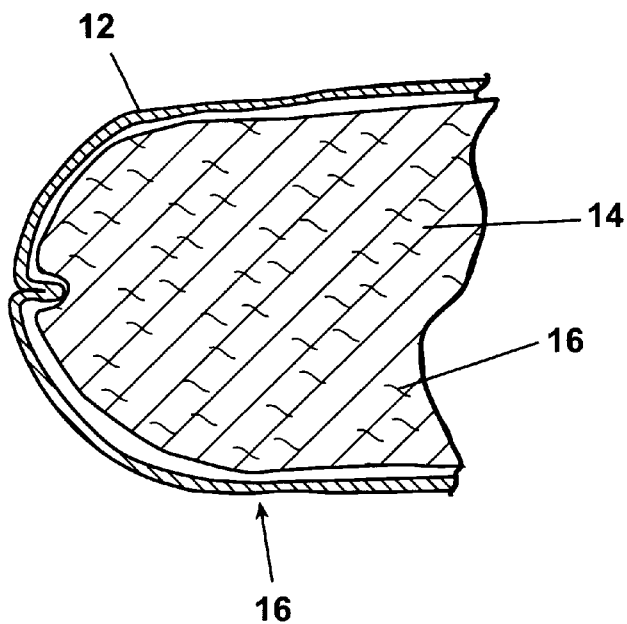
FIG. 3 is a sectional view of a first embodiment of a bedding article of FIG. 1 or 2.

As shown in FIG. 3, the bedding article 10 generally comprises an outer casing 12, an inner filling 14, and a microbe-inhibiting agent or property 16. The outer casing 12 can be fabricated from woven, non-woven, knitted, and nylon fabrics. Preferably, the outer textile casing 12 is fabricated from polyester or acrylic fabric as they both possess good natural microbial resistance and readily take up microbe-inhibiting chemicals. In another embodiment, the outer textile casing 12 is made from nylon. Another embodiment uses acetate, but is preferably incorporated with a microbe-inhibiting agent. Triacetate is generally preferred to acetate as it has higher natural microbial protections.

Figure 4:
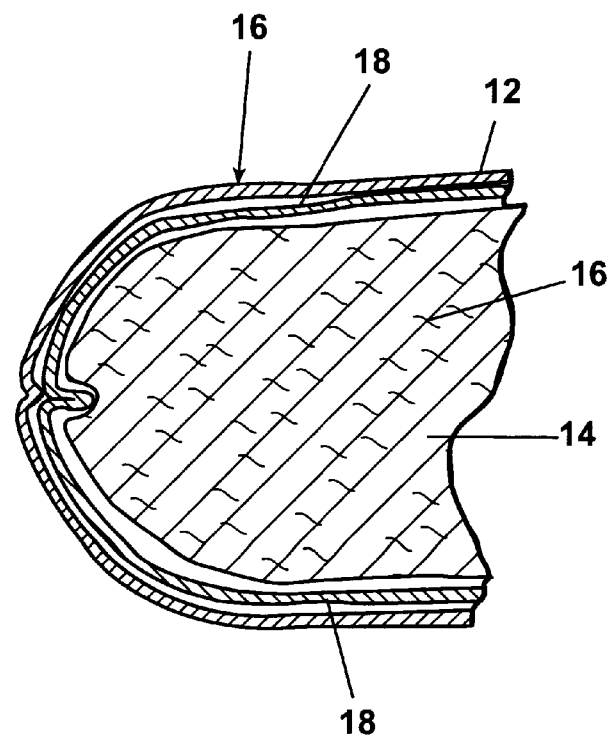
FIG. 4 is a sectional view of a second embodiment of a bedding article of FIG. 1 or 2 when viewed along line 3—3 of FIG. 1.

In a further embodiment, illustrated by FIG. 4, a microbe-inhibiting lining 18 is used in addition to a microbe-inhibiting cover 12. For example, one can attach a microbe-inhibiting lining 18 to the inner side of the cover 12, and containing the filling 14, of the bedding article 10. Further, one could construct an inner tick of a pet bed using such a microbe-inhibiting material. In using such a lining 18, it is generally preferred to employ materials with low permeability (e.g., microbe-inhibiting vinyl sheets); but when sewing is necessary, conventional fibers (e.g., microbecidally treated cotton or poly/cotton blend (are preferred for ease of manufacturing of the bedding 10.

More generally concerning the materials used for a lining or cover for a bedding article 10, the demands placed on the ethicacy of the microbe-inhibiting agents used are lessened by using materials that are naturally less inclined to harbor microbial proliferation. Thus, the natural microbial resistance of materials derived from cotton, flax (linen), and rayon fibers are particularly poor. Materials derived from acrylic, polyester, nylon, olefin, triacetate, rubber, and spandex fibers possess much better microbial resistance. Because microbial proliferation usually requires the presence of moisture, it is additionally attractive that the constituent material does not readily take up or absorb/adsorb water.

The degree to which fibers do take up or absorb/adsorb water is a function of the surface properties in the microstructure (e.g., porosity). Thus, one is generally interested in fibers and derived textiles that are poorly wetted by water and display a low moisture regain. These considerations guided the choices of preferred materials for the above embodiments.

It may be desired that the fabric comprising the cover 12 possess a softer feel, which may be provided by using a fabric that includes some fraction of cotton fiber. While cotton has a more natural microbial resistance, hydrophilic nature, and increased twice, these disadvantages are offset by blending with other fibers, particularly polyester. When cotton is used, however, it is preferably provided with microbe-inhibiting properties or the bedding article 10 itself is designed so that the microbe-inhibiting agents are transported to the cotton, as will be described in detail below.

In sum, whether the embodiment includes a lining, a cover, or both a lining and a cover, a preferred lining or cover is manufactured using materials derived from acrylic, polyester, and/or nylon fibers. Portions of the fabric may be constructed of cotton and/or acetate (or triacetate) fibers, which would portray the advantages described above. Some fraction of these materials in the preferred bedding article 10 are incorporated with microbe-inhibiting agents such as 2,4,4'-trichloro-2'-hydroxydiphenol (e.g., Triclosan) at the time of manufacture of the constituent fibers.

The inner filling 14 can be fabricated from foam or various synthetic or natural fibers; these fibers are generally composed of various synthetic or natural polymers. The foam materials are typically based on a polyurethane. The fibers are manipulated (cutting, crimping, etc.) to produce a material suitable for filling or to produce various yarns, textiles, woven structures and fabrics, and non-woven structures and fabrics. Fabrics comprising a "fluffy" or high-pile component attached to a backing material (e.g., artificial fleece, plush, etc.) are frequently employed in the manufacture of bedding articles for pets. Foam materials, especially based on polyurethane, are also used as a filling material and sometimes as an exterior material.

A common type of bedding article for a pet is as shown in FIG. 1. The outer cover 12 or outer containment structure is the surface which engages directly the pet. Access to the interior of the outer cover may be provided by a zipper 20 or by other equivalent means, or there may be no access (e.g., the article mat be permanently closed on all sides). The interior of the outer cover 12 contains the filling 14, which can comprise a variety of materials, including down, cotton, pelletized paper fiber, straw, saw dust, rice hulls, grass, feathers, or other natural or synthetic fibers, textiles, or pellet-type materials, or some combination. A variety of polymers, plastics, ceramics or glassy materials, or metals may be used as components comprising the synthetic fibers, textiles, or pellet-type materials. Often, especially if there is access to the interior, the interior filling is contained within an inner tick; and this inner tick, which is much like a permanently sealed cover material, is contained within the interior of the outer cover.

Figure 2:
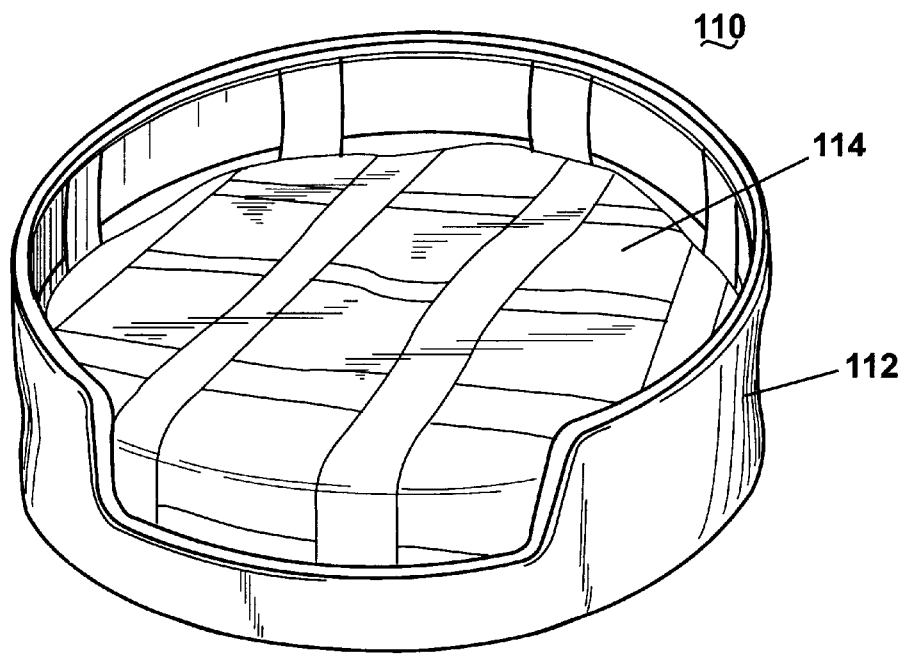
FIG. 2 is a perspective view of a second embodiment of a bedding article for a pet according to the invention.

An alternative bedding article 110 is as shown in FIG. 2, including the sidewall 112 and the base 114. The sidewall 112 may be constructed as a single section or piece of material that is generally continuous about at least a portion of the periphery of the base 114. A purpose of the sidewall 112 is to serve as a wall against which the pet may lean. A purpose of the base 114 is to serve as a mattress or cushion that insulates (thermally and physically) the pet from the underlying support surface. The base generally has an upper and a lower surface.

The sidewall 112 and base 114 may be constructed using a variety of materials and structures, including a soft-flexible foam core material formed in or cut into the appropriate shape(s); a hollow-type structure comprised of polyethylene or polypropylene; or a filled- or stuffed-type structure.

The bedding articles 10, 110, as described above, and their component parts, including covers and fillings, singly or in some combination, may be made to possess microbe-inhibiting properties following the teachings of the present invention. Depending upon cost considerations and the desired properties of the bed, the filler materials may be used singly or together in a variety of composite compositions.

One potential advantage of using synthetic materials for covers and fillers is that there is more flexibility in terms of the imparting of microbe-inhibiting properties to the materials. For example, one can incorporate a microbe-inhibiting agent in the material at many points during the manufacturing of the material. In addition, it is often easier to form synthetic materials into desired shapes and structures. For example, the characteristics of the filler may be adjusted so that properties such as bulkiness, softness, and thermal insulating behavior may be controlled within a desired range.

Covers are often important components of bedding-type articles for pets. A cover generally serves to enclose and protect the sidewall and/or the base. A single cover may enclose the entire structure; the base and sidewall may possess separate covers; or a cover may be omitted from one or more of the components of the bed. Covers may be removable, or they may be adhered to the component(s) which they cover. Alternatively covers may comprise a laminate of a soft outer material and an inner microbe-inhibiting layer, which laminate may be adhered to the components it covers. Covers may be made to have the desired microbe-inhibiting properties via post-treatment or by using microbe-inhibiting active raw materials in constructing the cover material.

For example, the cover can be constructed in whole or in part from vinyl, denim, or nylon fabric. Portions of the cover can also be constructed using a synthetic material which simulates fur, such as an artificial sheepskin fabric. In accord with the present invention, each of these materials, alone or in combination, may optionally be made to possess microbe-inhibiting properties and/or properties which aid in the effective cleaning of the materials.

One can also construct bedding articles for pets using resilient (e.g. layered, conglomerated, or cross-linked) non-woven fiber structures or foams in which some fraction of the fiber or foam possesses microbe-inhibiting properties. These may be simple articles without covers (the animal sits directly on the fiber or foam), or one can include a cover with an optional inner tick. For the non-woven fiber-based bed, one can use commercially available microbe-cidal filter material to construct the bed. In addition, microbe-cidal foams are commercially available.

Synthetic fiber-based materials used in making these bedding articles for pets may comprise a thermoplastic polymer or a blend of thermoplastic polymers. These materials can be provided with microbe-inhibiting properties in a variety of ways, including post-treating with a microbe-inhibiting agent or incorporating microbe-inhibiting agents into the materials during their manufacture. The latter is generally preferred.

Suitable polymers include polyolefin, acetate, and acrylic resins, nylon, polyethylene terephthalate (PET), and mixtures thereof.

Polyolefin resins selected from the group consisting of polyethylene and polypropylene are useful. Preferred here are low-density polyethylene resins such as Dow Chemical's "LDPE 640."

Acrylic polymers of particular utility for the present invention include those comprising acrylonitrile units and either vinyl acetate, methacrylate, or methyl methacrylate units. Optionally, other components may be included, e.g., to impart flame resistance to the polymers. Modacrylic polymers of particular utility in the present context are those comprising acrylonitrile, vinylidene chloride, and/or vinyl bromide units.

Foam-type materials are preferred in the present invention, due to their ease of manufacture, their ability to be formed in a variety of forms and shapes, and their low cost on a volume basis. They may be provided with microbe-inhibiting properties by including appropriate microbe-inhibiting agents in the materials during their manufacture or by treating the materials with such agents after their manufacture. Adhesion agents may be used to bind more effectively the microbe-inhibiting agents to the foam. Foam materials may be cut to the desired shape and then inserted into the cover material of the bedding article. The shaped foam can also serve directly as the bedding article, without a cover material. In this case, the foam is typically fabricated to possess a significantly higher density than in cases when the foam is inserted into a cover material.

Selection of Plasticizer

Although some polymers possess a significant degree of natural inhospitableness to microbial proliferation, they may lose this desirable property if they are processed using certain plasticizers. The plasticizers used in processing many polymers are digestible and/or degradable by microbes. If a plasticizer is to be used in processing materials used for constructing a bedding article for a pet, it is preferred to choose a plasticizer which does not diminish the natural microbe-inhibiting property of the polymer. Below are listed plasticizers which are resistant to fungal growth.

Plasticizers Resistant to Fungal Growth

Abietic acid; hydrog. methyl abietate; tri-n-butyl aconitate; triethyl aconitate; di-(2-ethylhexyl)adipate; di-(2-ethylhexyl)acetate; ethyl-o-benzyl benzoate; chlorinated diphenyls; chlorinated paraffins; tri-n-butyl citrate; triethyl citrate; 2-nitro-2 methyl-1,3-propanediol diacetate; dimethyl phthalate; di-n-propyl phthalate; diisopropyl phthalate; dibutyl phthalate; diisobutyl phthalate; diisodecyl phthalate; dihexyl phthalate; dicapryl phthalate; di-(2 ethylhexel) phthalate; di-(2 ethylhexyl) phthalate; dicyclohexyl phthalate; dicyclohexyl phthalate; and dibenzyl phthalate.

Non-Wovens

Some articles are the present invention may be made using non-woven fabrics. These are generally made from extruded continuous filaments or from fiber webs or batts strengthened by some form of bonding between or among fibers. The fibers may be bonded, e.g., by heating (including use of low-melting coatings), by adhesives, stitch-bonding or mechanical interlocking (e.g., needling).

A preferred base material is often polyester or olefin fibers or filaments; and preferred non-woven for the present invention is a very high-loft, low density type such as those used in filtration systems. These non-wovens may be prepared at large thickness (on the order of inches) and cut into appropriate shapes.

More traditional non-woven fabrics (e.g., non woven felt) may be used as cover materials in articles of the present invention.

In preparing microbe-inhibiting fibers, the microbe-inhibiting agents may be incorporated in a variety of ways, including adding the microbe-inhibiting agents to the melt or the spin dope from which the fibers are spun; or impregnating or otherwise treating the filaments as they are being stretched, washed, dried, cooled, solidified, or otherwise treated. One can also treat finished fibers by soaking or spraying in a solution containing a microbe-inhibiting agent.

When synthetic fibers are being used, it is preferred to add the microbe-inhibiting agents to the melt or the spin dope from which the fibers are spun (extruded). In this case, the microbe-inhibiting agent becomes an integral part of the fiber; and the durability of the resulting microbe-inhibiting efficacy is generally enhanced considerably. Phenol derivatives, especially 2,4,4'-trichloro-2'-hydroxydiphenol (sometimes known as Triclosan, Irgasan, Microban, or by other names) are particularly attractive. Organotins, especially Tri-n-butyltin maleate (as in Ultra Fresh DM-50), are also attractive.

In the case of fibers which are melt spun, it is important to ensure that the degradation temperature of the microbe-inhibiting agent is higher than the melt temperature. Because of the lower temperatures used, solution spinning methods are generally preferred for the manufacture of microbe-inhibiting fibers.

If the microbe-inhibiting agent is to be incorporated into a preformed fiber or tow, it is often preferred to do so when the fiber still possesses an open and/or porous structure. This is preferred when solution-spinning acrylic or modacrylic fibers, where the microbe-inhibiting agent may be applied to the filaments from the finish bath through which the filaments pass en route to the drying rolls. When the filaments are then processed on the drying rolls, the microbe-inhibiting agent is retained in the fiber. After the microbe-inhibiting agent is applied to the tow, care must be taken so that the microbe-inhibiting agents are not volatilized during subsequent processing.

In the case of melt-spun fibers, the microbe-inhibiting agents may be applied to the filaments either prior to or along with the spin finish application. When applied prior to the spin finish application, the microbe-inhibiting agents are preferably applied from an aqueous solution or emulsion thereof. A spin finish-containing agent may be applied to the filaments in a conventional manner, e.g., by passing the filaments over a metered finish applicator where a predetermined amount of finish is applied to the filaments.

Fiber to be used as fiber-fill may also be treated so as to possess microbe-inhibiting properties at the time it is incorporated into the containment structure by a blowing/filling machine. The blowing/filling machine may be constructed so as to spray, soak, or otherwise contact the fiber with the appropriate microbe-inhibiting treatment solution. For this application, Tri-n-butyltin maleate (Ultra Fresh DM-50) is a preferred agent.

It is important to note that post-treatment methods involve importantly different considerations when one is using a "strongly-bonded" type of agent. In the "diffusing" or "non-strongly-bonded" case, one immerses or otherwise exposes the materials to a solution containing a particular concentration of the agent. Generally, the agent diffuses into the material until its concentration in the material is comparable to the concentration in the solution, i.e., the treatment level of the material is essentially proportional to the concentration of the agent in solution; and the agent concentration in the solution is the primary controlling variable. In typical treatments, the agent in solution is not appreciably depleted; and the amount of material exposed to the treatment solution is not carefully monitored and is not considered a primary variable of the treatment process.

In the strongly-bonded case, however, the agent usually does not diffuse into the material (fiber, fabric, etc.); rather, it chemically reacts with the surface of the material. Here one attempts to arrange conditions such that most of the "reactable" agent present in the solution reacts with and bonds to the surface of the material being treated. Knowledge of the amount of material being treated is thus crucial in determining the treatment level; and the material amount, along with the agent concentration in solution, are considered controlling variables of the treatment.

As used herein, the "amount of material," means the "amount of reactable surface" of the material. For porous materials which can take up the solvent in their interiors (e.g., many fibers or fabrics), the mass of the material is often used as an indicator of the reactable surface area—i.e., one can specify an agent level in solution per unit weight of material being treated. For non-porous materials and/or materials which do not absorb the solvent being used (hard plastics, highly solvent-phobic materials), more direct knowledge of the reactable surface area is needed. The preferred non-diffusing (strongly-bonded) microbe-inhibiting agent is Dow Corning 5700 (3-trimethoxysilylpropyldimethyloctadecyl ammonium chloride).

The length of the cut fiber figures importantly in the blending process. It the fibers are too long, blending can be ineffective. If the microbe-inhibiting fiber is not homogeneously blended, the microbe-inhibiting efficacy of the resulting pet bedding article can be dramatically reduced. Filling using a blowing/filling machine can also become problematic with longer fibers (if the fibers are very long, hand filling can also be considerably more difficult). For articles of the present invention, the cut length of the fiber should be between 0.1 and 8 inches, preferably between 0.3 and 5 inches, and most preferably between 0.4 and 3.5 inches.

When fiber blends are used, it is preferred that both the microbe-inhibiting fiber and the non-microbe-inhibiting fiber both possess the same cut length.

Microbe-inhibiting fabrics may be constructed by weaving, knitting, or otherwise forming the fabric from fibers which possess the desired microbe-inhibiting properties. Alternatively, the fabrics can be post treated via spray-treating or by using a padding system such as are common in the art of textile finishing. For post treatment, Tri-n-butyltin maleate (as in Ultra Fresh DM-50) is a preferred diffusing microbe-inhibiting agent (at fabric pick-up about 0.1%–0.5%); and 3-trimethoxysilylpropyldimethyloctadecyl ammonium chloride (as in Dow Corning 5700) is a preferred strongly bonded microbe-inhibiting agent (at fabric pick-up about 0.08%–0.15%).

The preferred means for obtaining microbe-inhibiting foams is to include a microbe-inhibiting agent in the formulation of one of the foam precursors (i.e., before the material is foamed) A preferred microbe-inhibiting foam is obtained by adding Ultra Fresh DM-50 to the polyurethane foam formulation before foaming (typically in amounts ranging from 0.04% to 0.6% relative to the total weight of the formulation). Another preferred means is to use Dow Corning 5701 (a reactive silane quaternary ammonium compound, which works much like Dow Coming 5700). This agent is also added into the formulation of the foam before foaming (typically in amounts ranging from 0.1% to 1.2% relative to the amount of polyol).

It would be a further benefit to articles of the present invention that they resist the proliferation of mites, fleas, ticks, and other pests. One means for inhibiting the ability of such pests to proliferate in the interior of the articles of the present invention is to use outer fabrics possessing very tight weaves (so the pests cannot pass through the interstices or pores of the fabric. Another means, particularly efficacious for inhibiting the proliferation of dust mites, is to use the microbe-inhibiting agent Ultra Fresh DM-50 in treating or preparing the fabric, foam, fiber and/or other materials used in the article (this agent appears to possess the ability to limit dust mites).

Microbe-Inhibiting Agents

A wide variety of chemicals may be used as microbe-inhibiting agents in the present invention. For listings of chemical additives which can impart anti-microbial properties, see the *Plastics Additives and Modifiers Handbook* (pp. 338–350, J. Edenbaum, Ed., Chapman and Hall, Great Britain, 1996); *Plastics Handbook* (Modern Plastics, 1994, McGraw Hill); and *The Practical Application of Disinfection and Sterilization in Health Care Facilities* (J. C. Cokendolpher and J. F. Haukos, American Hospital Association, Chicago, Ill., 1996).

Nearly all heavy metals possess some degree of microbe-inhibiting activity (especially of the anti-fungal kind). Copper naphthenate, e.g., may be applied from a solvent bath, optionally with additional microbe-inhibiting agents in the same bath. Alternatively, fabric or fill can be impregnated with a copper salt dissolved in ammonia, and then treated with napththenic acid. Other useful copper salts include hydroxynaphthenate, stearate, tallate, oleate, resinate, acrylate, furoate, antimonate, and chloracetate.

Chlorine dioxide, typically in aqueous solution, also possesses microbe-inhibiting properties, and it may be used to impart such properties to bedding articles for pets. The articles may be soaked in the solution or may be treated topically with the solution, or constituents of the articles may be treated with the solution. Chlorine dioxide is attractive because it may be obtained in a stabilized form in which it is non-toxic. It is used in toothpaste and mouthwash for humans, and it is a particularly preferred anti-microbial agent for the present invention.

The microbe-inhibiting properties of quaternary ammonium compounds are well-known; and several examples are given below. They may be used alone or in conjunction with other microbe-inhibiting agents, preferably in conjunction with adhesion promoters, especially alkoxysilane coupling agents. A preferred example is Dow Corning 5700 microbe-inhibiting agent (3-trimethoxysilylpropyldimethyloctadecyl ammonium chloride). Additional agents suitable for use in this context include cetylbenzyldimethyl ammonium chloride, tertiary octylphenoxyethoxyethylbenztyldimethyl ammonium chloride, and lauryl pyridinium chloride.

Suitable other quaternary ammonium compounds include polyamniopropyl biguanide, 1-(3-chlorallyl)-3,5,7-triaza-1-azoniaadamantane chloride (available under the trade name Dowicil 200 from Dow Chemical). Still other suitable quaternary ammonium compounds are included in the next section.

Effective organic sulfur compounds include the microbe-inhibiting organic preservatives containing 3-isothiazolone groups and sodium pyrithone. Halogenated compounds suitable for use in the present context include 5-bromo-5-nitro-1,3-dioxane (available from Henkel under the trade name, Bronidox); 2-bromo-2-nitropropane-1,3-diol (available from Inolex under the trade name, Bronopol); 1,1'-hexamethylene bis 5-(p-chlorophenyl) biguanide (commonly known as chlorhexidine) and its salts; 1,1,1-trichloro-2-methylpropan-2-ol (commonly known as chlorobutanol); 4,4'-(trimethylenedioxy) bis-(3 bromobenzamidine) diidethionate or dibromopropamidine. The addition of thiazole derivatives, specifically 2-mercaptobenzothiazole, is useful. Thiazoles can be used effectively in mixed combination with other chemicals such as the quaternary ammonium salts and selected metal derivatives, e.g., of mercaptobenzothiazole, in which the metal itself possesses anti-microbial properties.

Suitable phenyl and phenoxy compounds include 4,4'-diamidino-alpha,omega-diphenoxypropane diisethionate (commonly known as propamidine isethionate); and 4,4'diamidino-alpha,omega-diphenoxyhexane diisethionate (commonly known as hexamidine isethionate). Other examples are benzyl alcohol 2-phenylethanol, and 2-phenoxyethanol.

Chlorinated phenolic compounds are generally preferred for incorporation into the bulk of many materials. 2,4,4'-trichloro-2'-hydroxydiphenol is especially attractive and, for reasons discussed herein, is a highly preferred agent in the present invention. Other possible chemical names for this agent are chloro-2-(2,4-dichlorophenoxy)phenol; 5-chloro-2-(2,4-dichlorophenoxy)phenol; or 2,4,4'-trichloro-2'-hydroxydiphenyl ether. Trade or common names which are comprised primarily of the agent are Triclosan, Irgasan, Irgasan DP-300, Microban, Microban B, Lexol 300, and others. The Ultra Fresh family of agents, solutions, and materials, available from Thomson Research Associates, often include significant amounts of this Triclosan-type additive (sometimes, along with quaternary ammonium compounds and/or tributyltin oxide compounds).

DM-50 (Thomson Research Associates) is a preferred form of the preferred organotin agent, tri-n-butyltin maleate.

Another preferable microbe-inhibiting agent is known by the trade name, Intersept. It is a complex of polysubstituted imine salts and trialkyl phosphate esters with free alkylated phosphoric acid. It is relatively non-toxic; and it has been used as an anti-microbial finish on many building materials.

A further preferred type of microbe-inhibiting agent is typified by the MicroFree brand of particulates (available from DuPont). These particulates generally comprise a core particle (zinc oxide, titanium oxide, or barium sulfate) over which is coated a microbe-inhibiting active layer (silver, copper oxide, and/or zinc silicate). A barrier layer (to control the rate of release of the active component) and a dispersion coating (to facilitate dispersion of the particles in host materials) are included on top of the active layer. The particles range from about 0.3 $\mu$m to 1 $\mu$m in size. They can be incorporated into many resin systems for plastics processing, into the dope before fiber spinning, and into many coating systems for post-treatment. Good microbe-inhibiting efficacy can be imparted to various materials using these particles; and the resulting materials are generally non-toxic, very stable, and cost effective.

The microbe-inhibiting agent chosen depends on many factors, including toxicity; the desired method of incorporation; material compatibility issues; and economic considerations.

Compounds and Solutions with Selected Concentrations

Below is a listing of chemical compounds with demonstrated effectiveness for various microbe-inhibiting applications. The effectiveness of each depends upon its concentration, the presence and concentrations of other microbe-inhibiting agents, the nature of the surface, the temperature, and the overall pH of the solution, etc.

Most of the microbe-cidal chemicals listed are followed by a representative effective concentration range. These concentration ranges are meant to be typical and representative; the concentration actually used may vary with other conditions of the treatment, with the nature of the host material, with the concentrations and efficacies of other microbe-cidal agents (or microbe-starving or microbe-inhibiting properties) present, and with the degree of toxicity allowable.

As used herein, all concentrations given in units of percent are understood to be weight percent (unless otherwise stated).

The agents listed in this section may be used as additives in polymers, but many may also be used effectively in liquid treatment solutions. The preferred concentrations depend on a variety of factors, including the type of polymer, its required physical and chemical properties, the degree of toxicity allowable, and the environment in which the bedding article is to be used. Unless otherwise stated, when concentrations are given below, they correspond to the percentage of the total plastic or liquid formulation which is the microbe-inhibiting agent. In some cases, a preferred material is given with which the additive is compatible and effective. The chemical compounds (and in some cases broad categories of compounds) and typical concentrations are as follows:

Copper-8-quinolinolate (0.2–4%, in, e.g., vinyl); mercaptan (0.2–4%, in, e.g., vinyl); tetramethylthiuram disulfide (0.4–4%, in, e.g., vinyl or cellulose nitrate); copper napthenate (0.2–4% in, e.g., PVC or PVA); pentachlorophenol (1–20%, in, e.g., lacquer or cellulose nitrate); phenyl mercuric formate (0.05–10%, in, e.g.,nylon); pentachlorophenol (0.2–4%, in, e.g., celluose nitrate); 10,10'-oxybisphenoxarsine (OBPA) (0.005–2%, in a variety of plastics, including vinyl, PVC, and others; sometime sold under trade names, "Intercide" or Vinyzene); organotins (0.005–2%, in, e.g., PVC) (examples of organotins are, e.g., bis (tri-n-butyltin)sulfosalicylate (0.25–0.5% of plasticizer, used in e.g., PVC), or the preferred tri-n-butyltin maleate (0.005–1%, in, e.g., urethanes, polypropylene, paint-compounds); brominated salicylanilide (0.04–1%, in, e.g., polyethylene).

Phenolics, particularly especially chlorinated phenolics (hexachlorophene, dichlorophene, p-chlorometacresol, p-chlorometaxylenol, o-benzyl parachlorophenol, and o-phenylphenol), and especially 2,4,4'-trichloro-2'-hydroxydiphenol (0.05–10%)—the latter has been incorporated successfully into a number of plastics and other products; it may be written as is 2,4,4'-trichloro-2'-hydroxydiphenol, or as 5-Chloro-2-(2,4-dichlorophenoxy) phenol; and may be referred under the names Triclosan, Irgasan, Microban, Microban B, Lexol 300; quarternary ammonium compounds (e.g., quarternary ammonium napthenate (0.5–6% of the plasticizer, used, e.g., in PVC); blends of substituted ammonium salts of alkylated phosphoric acids mixed with a free alkylated phosphoric acid (especially complexes of polysubstituted imine salts and trialkyl phosphate esters with free alkylated phosphoric acid)—0.1–4% of the coating used; Fungitrol 11 (N-trichloromethylthiopthalimide powder); Vancide 89 (N-(trichloromethylthio)-4-cyclohexene-1,2-dicarboximide, powder); Microchek 11 (2-N-octyl-4-isothiazlin-3-one, liquid); Omacide (zinc pyrithione); Preventol (N-(fluorodichloromethylthio)pthalamide); Apacider (silver hydroxyapatite); and Vinyzene SB-129 contains as an active ingredient N-(2-Methyl-1-naphthyl) maleimide.

Bedding Articles Having Materials Exhibiting a "Zone of Inhibition"

Figure 5:
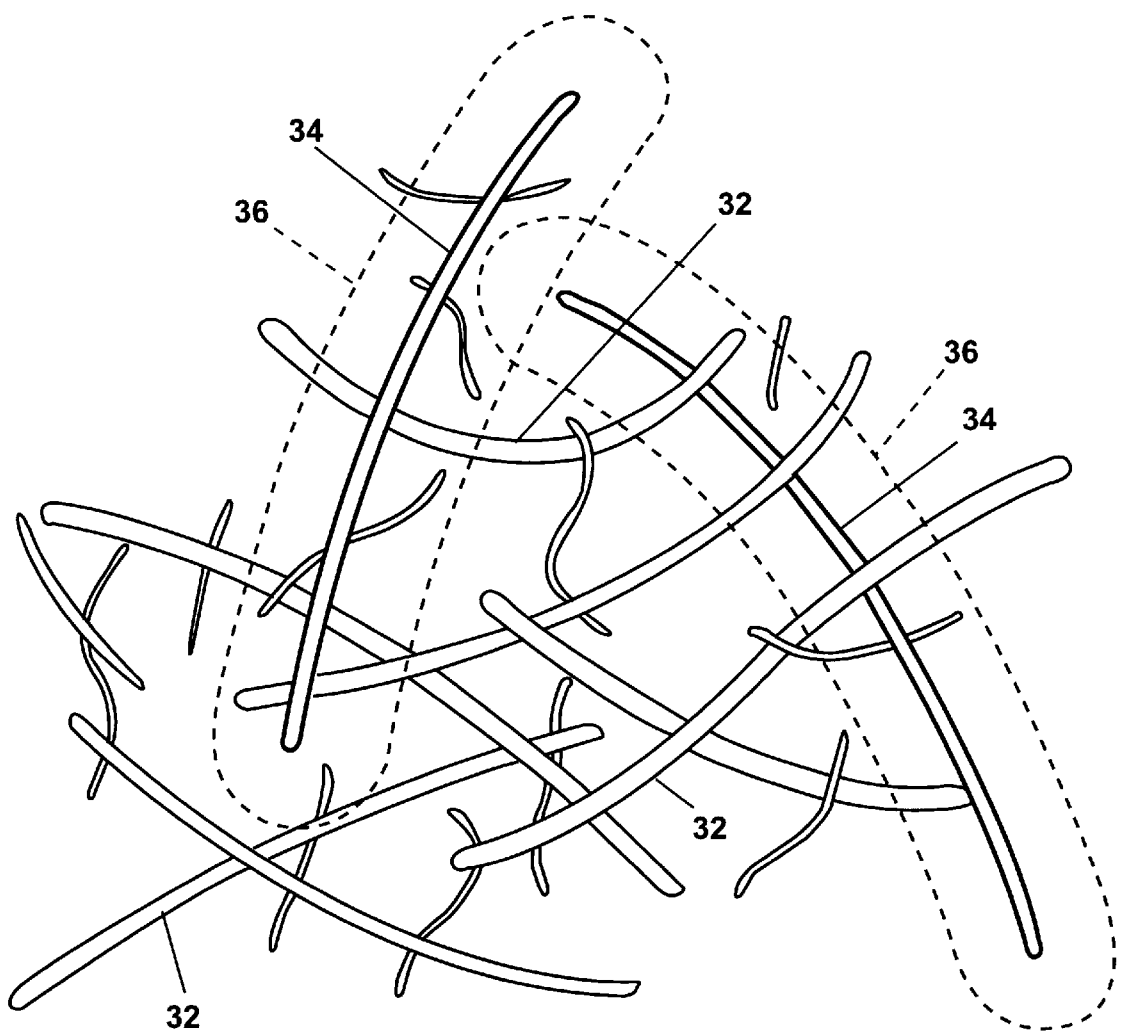
FIG. 5 illustrates a fiber assembly for the articles of FIGS. 1–4 including initially microbe-inhibiting fibers blended with initially non-microbe-inhibiting fibers.
Figure 7:
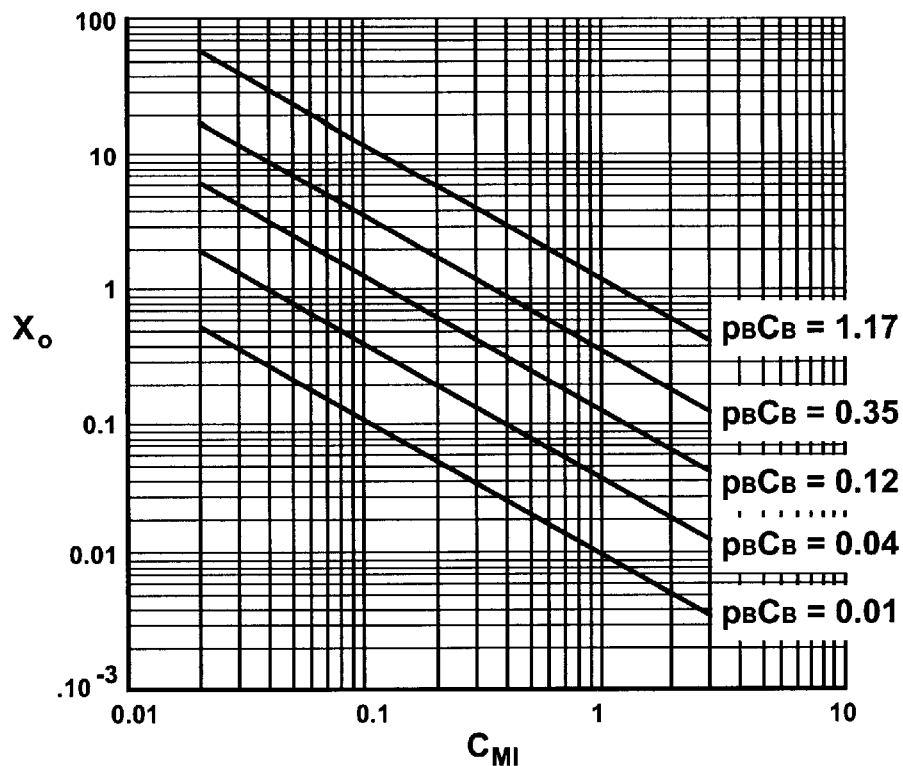
FIG. 7 is a graph displaying the volume fractions of the containment structure according to the invention within a zone of inhibition as a function of the volume fraction of a containment composed of microbe-inhibiting fibers.

Some microbe-inhibiting materials contain an agent which can diffuse out of the material. Such materials generally exhibit a significant "zone of inhibition," whereby microbial growth is effectively inhibited some distance away from the material (e.g., see *Plastics Additives and Modifiers Handbook*, pp. 338–350). In these materials, the agent is not fully bonded to or otherwise trapped in the material, and it can be transported from the material into its surroundings. FIG. 5 demonstrates the zone-of-inhibition, shown in dashed lines 36, as surrounding the microbe-inhibiting fibers 34, and encompassing regions containing the initially non-microbe-inhibiting fibers 32.

In other cases, the microbe-inhibiting agents may be strongly bonded to or otherwise trapped within the host material. The zone of inhibition is very small for these materials; and microbes are killed or otherwise inhibited only by coming into direct contact with the material.

The behavior of the zone-of-inhibition 36 has profound effects on the design of efficacious microbe-inhibiting bedding articles for pets. For example, if the fiber used as the filling of a bedding article for a pet has been provided with a strongly bonded microbe-inhibiting agent, then the zone of inhibition is very small; and the filling should be composed almost exclusively of the microbe-inhibiting fiber. In addition, the microbe-inhibiting fiber will not spread its microbe-inhibiting efficacy to the cover; and if any protection is desired on the cover, it must be separately supplied.

If the fiber is provided with a diffusing microbe-inhibiting agent, however, the design is more complicated. It is preferred to use a fiber blend in which only a modest fraction of the fiber is provided with microbe-inhibiting properties. Over time, and accelerated by use, the agent will diffuse to the fibers which were not initially provided with microbe-inhibiting properties. In addition, if the agent is suitably mobile, it may impart a microbe-inhibiting characteristic to the cover as well. In this case, one must properly consider the interplay between the characteristics of the zone of inhibition (its extent, shape, decay characteristics, and dependence on the surrounding fiber packing density), the rate of depletion of the microbe-inhibiting agent from the fiber (and how this impacts the characteristics of the zone of inhibition), and the distribution of the microbe-inhibiting fiber within the total filler.

If the agents are extremely mobile and weakly attached to the host material, they will readily and rapidly diffuse to contiguous materials which contain smaller concentrations of the agents; and this will occur until the overall concentration approaches uniformity. In this limit, as long as there is extensive contact among the fibers comprising the filler, the zone of inhibition is essentially limitless in extent; and, for the bedding article to be provided with microbe-inhibiting properties, one must only ensure that there is enough agent present in the fibers which initially contain the microbe-inhibiting agent that the overall concentration will remain at a sufficient microbe-inhibiting level for the desired lifetime of the article. Thus the important parameter in designing articles in this case is the total concentration of the microbe-inhibiting agent. Issues related to the design of yams and fabrics in this limit are discussed in U.S. Pat. No. 3,959,556 and U.S. Pat. No. 4,842,932.

An important distinction between fiber as used as filling in the present invention, as opposed to fiber as used in yams and fabrics of the prior art, is that the fiber used as filling in the present invention is typically the component of the interior of a containment structure within which the great majority of the space (by volume) is typically comprised by air.

As mentioned above, the prior art deals with cases in which the diffusing microbe-inhibiting agent easily leaves its initial host and permeates the entire space of the yarn or fabric of which it is part (i.e., an effectively infinite zone-of-inhibition). In systems of the present invention, however, there are typically restrictions on the transport of the microbe-inhibiting agents and/or the agents possess a significant degree of attachment to their hosts; and a finite zone-of-inhibition is present. In this case, for adequate microbe-inhibiting protection, one must ensure at the very least that that the microbe-inhibiting fibers and their associated zones of inhibition comprise a sufficient volume fraction of the containment volume; and the prior art is silent in this regard.

Designing Bedding Articles Having a Microbe-Inhibiting Agent or Property

In the present invention, there are two basic approaches to the design of effective microbe-inhibiting bedding articles: 1) An empirical approach, in which key design variables are identified; and appropriate ranges of and relationships among these variables are determined with respect to the effectiveness of the microbe-inhibiting character of the so-designed articles; and 2) A direct approach, in which the effective extent of the zone-of-inhibition is determined experimentally under conditions which simulate actual use of the article; and the appropriate ranges of and relationship among design variables are thereby calculated using a mathematical model.

One means for determining whether a given design displays the desired degree of microbe-inhibiting efficacy is as follows. Construct the bedding article according to the design; soak the article in a fluid containing microbes (e.g., tap water) for five minutes; transfer the article to the interior of an air-tight bag; heat at a desirable incubation temperature (e.g., 37° Celsius) for a desirable time (e.g., 8 days); and have another person open the bag and grade the severity of the odor on a scale of 1 (bad) to 3 (no odor). An effective design produces no noticeable odor.

It is necessary to determine several parameters of the components of the bedding article for a pet:

1. The volume of the cover or containment structure, $V_c$. This is the total volume which can be held within in the cover or containment structure. This can be determined as follows: fill the cover with small plastic beads; empty the beads into a large cylindrical container from which one may read the volume; and read the volume.

2. The densities of the fibers. It is necessary to know the fiber densities so that one may calculate the fiber volume from the fiber mass. If a hollow-type fiber is being used, it is usually advisable to use the effective or average density.

3. The radius of the fibers, $r_f$. The denier of the fiber may be used to estimate the effective fiber radii, $r_f$, as $$r_f = \sqrt{\frac{denier}{9\pi \cdot 10^5 \cdot \rho}}$$

where $\rho$ is the average density (in units of gm/cm³) of the material comprising the fiber. If the fibers are roughly circular in cross section, $r_f$ should correspond closely to the average physical radius of the fibers. If the fibers are decidedly non-circular in cross-section, $r_f$ is an effective averaged radius (i.e., the relevant behavior is much as if the fibers were of circular cross-sectional radius, $r_f$). The use of the above becomes increasingly accurate for fibers which are more circular in cross-section and which possess a narrower distribution in cross-sectional size. If the fibers are hollow, the proper equation is somewhat more complicated; but one can calculate the radius using information supplied by the manufacturer.

After the above parameters are obtained, one can proceed to the design of the microbe-inhibiting article. There are several key variables which must be considered in designing the article:

1. The volume fraction, $x_o$, of initially microbe-inhibiting fiber. This is equal to the total volume of initially microbe-inhibiting fiber, $VMI_o$, divided by the total volume of the containment structure.

2. The average concentration of the microbe-inhibiting agent, $C_{MI}$, within the initially microbe-inhibiting fiber.

3. The fiber blend volume fraction, $\rho_B$. This is the volume fraction of the containment structure which is comprised of fiber of any kind. The fraction of the fiber blend that is composed of initially microbe-inhibiting fiber, $f_{MI}$:

$$f_{MI} = \frac{x_o}{\rho_B}$$

$C_{MI}$ is used to calculate the average blend concentration, $C_B$, as $$C_B = C_{MI} f_{MI}$$

$C_B$ would be the concentration of the microbe-inhibiting agent in the entire blend if the agent were to diffuse and become completely homogeneous throughout the blend (i.e., it is the average concentration of the microbe-inhibiting agent throughout the blend). If protection throughout the fiber blend is to be obtained, this value must be above the minimum efficacy level (sometimes referred to as a "minimum inhibitory concentration) for the particular microbe-inhibiting agent used.

Empirical Method

In designing effective microbe-inhibiting articles using a filling, where the filling possesses microbe-inhibiting properties, the design parameters of the fill must be chosen properly. The three key design variables are $x_o$, $C_{MI}$, and $\rho_B$. The variables $x_o$ and $f_{MI}$ must be sufficiently large that the initially microbe-inhibiting fiber can "spread" its inhibitory qualities throughout at least a predominant fraction of the entire blend, and preferably to the cover material as well; but not so large that the cost becomes prohibitive. $C_{MI}$ must be sufficiently large that there is enough microbe-inhibiting agent in the initially microbe-inhibiting fibers to spread to the initially non-microbe-inhibiting fibers (and optionally to the cover material) and still maintain a concentration that exceeds the minimum inhibitory concentration. $\rho_B$ must be sufficiently large that the microbe-inhibiting efficacy can spread effectively throughout the article. If, for a given $x_o$ and $f_{MI}$, $\rho_B$ is too small, the fibers will not be intermingled sufficiently, and the agent will not be able to diffuse effectively. If $\rho_B$ is too large, the relative motion of the individual fibers will be severely restricted, and the spreading of the microbe-inhibiting agent, which is facilitated by such motion, especially during vigorous use of the article, will be curtailed.

In determining the appropriate design parameters, the following design equation relates several of the key parameters:

$$\rho_B C_B = C_{MI} \chi_o \quad (1)$$

It is generally necessary that $C_B$ be much greater than the minimum inhibitory concentration. This is because, unless the agent is extremely mobile (which is not desirable due to durability concerns), the agent does not homogenize. For a considerable period of time, it retains notably higher concentrations near the source (initially microbe-inhibiting)

fibers. Thus, although $C_B$ is the average concentration in the fiber assembly, much of the assembly will be at a significantly lower concentration.

From tests using 2,4,4'-trichloro-2'-hydroxydiphenol, which is representative of diffusing microbe-inhibiting agents, the following design parameters were determined:

1. $C_B$ should be greater than 0.001%; preferably greater than 0.01%; and most preferably greater than 0.05%.

2. $\rho_B$ should be between 0.1% and 15%; preferably between 0.6% and 10%; and most preferably between 1% and 8%.

3. Once $C_B$ and $\rho_B$ are selected, the left-hand side of Eqn. (1) is determined; and $C_{MI}$ and $x_o$ are picked so that they are consistent. FIG. 2 shows $x_o$ as a function of $C_{MI}$ for several values of the $\rho_B C_B$-product (in units of %$^2$) For a particular desired $\rho_B C_B$-product, one can determine the appropriate $x_o$ to use for a given $C_{MI}$ (or vice-versa).

It should be noted that $C_{MI}$ cannot be arbitrarily large; it must be below a value at which the incorporation of the agent causes significantly detrimental effects to the mechanical or chemical stability or integrity of the fiber.

For a given $C_B$, it is preferred that $f_{MI}$ be as large as possible (its maximum value is one), i.e., $C_{MI}$ be as low as possible. For example, it is preferable to have a fiber blend comprising 50% initially microbe-inhibiting fiber with an agent concentration of 0.25% rather than a blend comprising 25% initially microbe-inhibiting fiber with an agent concentration of 0.5%. The larger $f_{MI}$ is, the less one needs to rely on diffusion of the microbe-inhibiting agents. Preferably $f_{MI}$ is between 0.3 and 4.5%.

Zone-of-Inhibition Method

This method requires estimating the effective extent(s) of the zone-of-inhibition, $R_{ZI}$. It should be noted that the ranges of $R_{ZI}$ are essentially phenomenological parameters. They are best measured under conditions similar to those present during use of the bedding article. Means for conducting such measurements are given below.

The zone-of-inhibition is represented in FIG. 5 by the region within the dashed lines surrounding the black (initially microbe-inhibiting) fibers. It is seen that the zone encompasses regions of the initially non-microbe-inhibiting fibers.

For larger materials, the zone of inhibition is often reported simply as a distance—without any reference to the size of the material. For fine fibers, however, the effective zone of inhibition can diminish with the size of the fiber. The physics of the zone of inhibition is complex, but its diminishment in finer fibers may be seen as due in part to the diminished capacity (defined as the total amount of agent that can leach from the fibers) of finer fibers. Values of the extent of the zone of inhibition typically reported for large samples are generally not appropriate for fine fibers. Further, standard tests for the zone of inhibition examine the extent of the inhibition into a relatively solid material (e.g., agar gel). In a stuffed bedding article, one is interested in the zone of inhibition as it diffuses into the surrounding fibrous medium.

When a fiber provided with a diffusing microbe-inhibiting agent is combined with conventional fiber, it is generally desired that nearly all the fibers be within the zones of inhibition of the initially microbe-inhibiting fibers. One can obtain an estimate of the fraction of the entire blend, $\zeta$, which is within a zone of inhibition by making an analogy to the Formal Theory of Phase Transformations (e.g., see J. W. Christian, *The Theory of Transformation in Metals and Alloys*, Pergamon Press, 1975). This theory describes the volume fraction of a material that has undergone a phase transformation.

If only a few initially microbe-inhibiting fibers are within an initially non-microbe-inhibiting fiber assembly, the total volume within a zone of inhibition is given simply by adding up the volumes of the zones-of-inhibition of the few fibers. When there are sufficiently many initially microbe-inhibiting fibers that the zones-of-inhibition start to overlap (which is a situation desirable in the present invention), it is necessary to "discount the excluded volume."

As a rule-of-thumb, for fibers (i.e., long and thin structures), the fraction of the entire blend, $\zeta$, that is within a zone of inhibition can be estimated as $$\zeta \approx 1 - \exp(-(1+\alpha)^2 \chi_o) \qquad (2)$$

where $$\alpha = \frac{R_{ZI}}{r_f} \qquad (3)$$

If $\zeta$ is close to unity, nearly all the conventional fiber is within the zones of inhibition of the initially microbe-inhibiting fiber.

For easy application to use with a wide variety of fibers, the effective extent of the zone of inhibition is represented by the dimensionless parameter, $\zeta$, which is equal to the ratio of the radial extent of the zone of inhibition, $R_{ZI}$, to the effective radius of the fibers, $r_f$.

The effective radial extent of the zone of inhibition, $R_{ZI}$, can be estimated by a variety of means. A preferred means begins with the preparation of a blend comprising the initially non-microbe-inhibiting fiber and a small amount (e.g., less than 1% by volume of the entire blend) of microbe-inhibiting fiber. The blend is then placed on a flat surface and spread somewhat, trying to maintain as much as possible the packing density of the fibers at a level comparable to that which is used in the end application. The entire sample is then inoculated with a desired test organism, and the sample is stored for a period of time necessary for the organism to grow appreciably in areas which are not close to microbe-inhibiting fiber (a control experiment, comprising only non-microbe-inhibiting fiber and the inoculating organisms, is performed simultaneously). The sample is then viewed using a microscope, and the effective range of inhibition is noted. Preferably, several measurements should be performed to ensure that one is measuring the range of inhibition accurately. If the degree of microbial growth is insufficient at reasonably long experimental time scales, one can perform the experiments with the fiber blend situated in contact with a known nutrient material (e.g., agar), preferably immersed in the nutrient material (e.g., place the fibers on an agar surface, inoculate, and then deposit more agar on top). Alternatively, for the non-microbe-inhibiting fiber in the blend, one can use a fiber which is known to be particularly susceptible to proliferation of the microbe(s) of interest.

$R_{ZI}$-values obtained by means described above will tend to be conservative, i.e., the "true" values may be somewhat larger. This is because use of the article generally involves mechanical stresses which tend to spread the MI efficacy throughout the bedding article. A static measurement, such as that described above, neglects this.

Directly measuring $R_{ZI}$ can be time-consuming; and the accuracy can sometimes be questionable. It is therefore sometimes preferable to treat $R_{ZI}$ as a phenomenological parameter, i.e., to determine the microbe-inhibiting efficacy on actual articles, and then to back-infer $R_{ZI}$. The determined $R_{ZI}$ can then be used for optimization of the actual design.

Equation (2) is more accurate when $x_o$ is not too large (i.e., less than about 0.6). It also applies more straightforwardly in cases where the fibers are packed more densely. Furthermore, it is generally preferred that, and the equation applies best when, the initially microbe-inhibiting fiber is distributed homogeneously throughout the fiber blend. This can be brought about be mixing the blend well and optionally by providing the fibers with anti-stick and/or anti-static properties.

Figure 6:
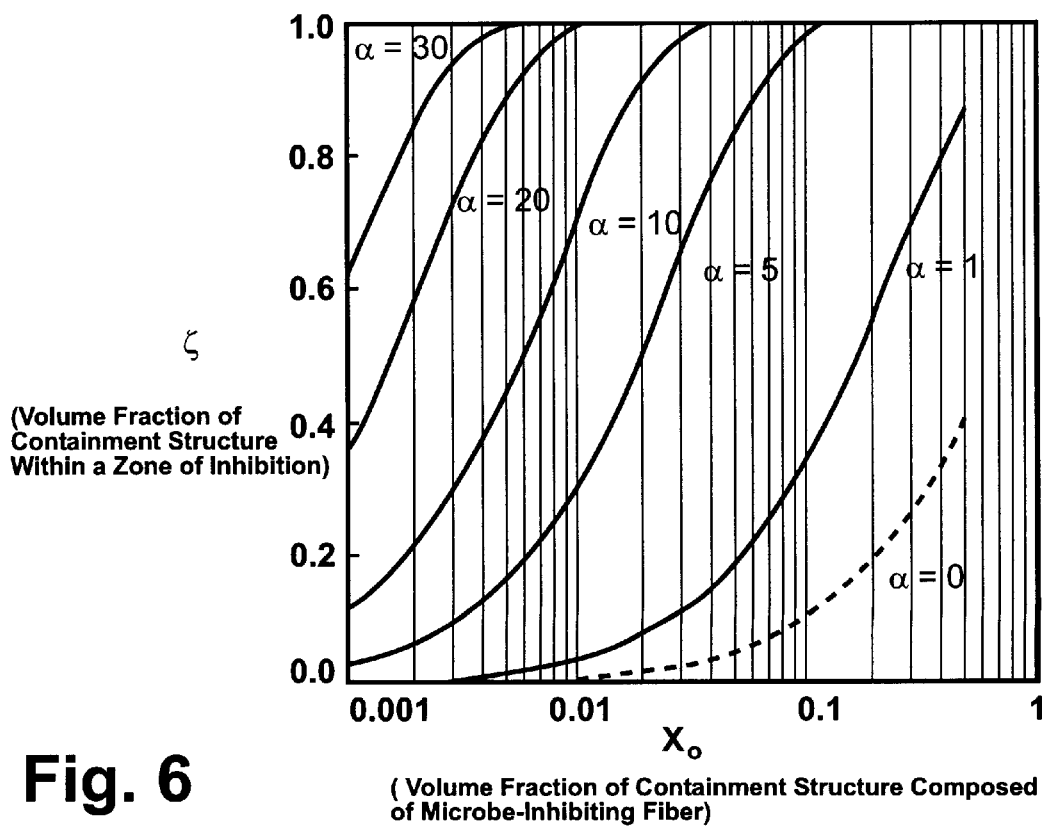
FIG. 6 is a graph displaying the volume fraction of a containment structure according to the invention composed of microbe-inhibiting fibers as a function of the concentration of the microbe-inhibiting agent in the microbe-inhibiting agent.

FIG. 6 is a plot of $\zeta$ (the estimated volume fraction of the interior of the containment structure which is within a zone of inhibition) vs. $x_o$ (in dimensionless units) for different values of $\zeta$ also in dimensionless units) $x_o$ is the volume fraction of the interior of the containment structure which is comprised of initially microbe-inhibiting fiber; and $\zeta$ is the ratio of the effective radial extent of the zone of inhibition to the effective fiber radius. Note that a log-scale is used for the $x_o$-axis.

Bedding articles for pets may also be made from containment structures which are filled with particulate filling materials, with foam materials, or with combinations of these with fibrous materials. For example, one can use a particulate material which is provided with diffusing microbe-inhibiting properties and combine it with conventional non-microbe-inhibiting fiber; or one can mix a foam material in which has been incorporated a microbe-inhibiting agent with a fibrous material.

If the microbe-inhibiting filling material (or some fraction thereof) is more particulate (i.e., three-dimensional) than fibrous, the rule-of-thumb for calculating the fraction of the containment volume that is within a zone of inhibition of the particulate microbe-inhibiting filling material is $$\zeta \approx 1-\exp(-(1+\alpha)^3 \chi_o) \quad (1)$$

where $$\alpha = \frac{R_{ZI}}{r_s} \text{ and } x_o = \frac{VMI_o}{V_c} \quad (2)$$

Here $R_{ZI}$ is the effective radial extent of the zone of inhibition for the microbe-inhibiting fibers used; $r_s$ is the effective radius of the microbe-inhibiting particles used; $VMI_o$ is the volume of microbe-inhibiting particles used in the blend; and $V_c$ is the volume of the interior of the filler containment structure (e.g., the inner ticking of a fiber-filled pet bed).

If the particles are roughly spherical, $r_s$ corresponds to their average radius. If the particles are appreciably non-spherical, $r_s$ should be interpreted as the effective average radius of the particles (i.e., the relevant behavior is much as if the particles were spherical with radius, $r_s$). Estimates of $r_s$ may be obtained by various means, including direct observation using a microscope. $R_{ZI}$ and $VMI_o$ may be obtained in manners similar to those used for fibers (see above). Considerations similar to those for fibers (see above) apply with regard to the relationship between the fineness of the particles and the effective radial extent of their zones of inhibition. $V_c$ is obtained in the same manner as in the case where microbe-inhibiting fibers are used.

In practice, the radius of the effective zone of inhibition will diminish with time as the diffusing microbe-inhibiting agent is depleted. The depletion rate is characteristic of the material and the microbe-inhibiting agent used; and it will increase with the packing density and the frequency and extent of washing and or abrasion.

It is preferred to construct microbe-inhibiting stuffed bedding articles such that ζ is between about 0.5 and 1. It is more preferable to construct such articles such that ζ is between about 0.8 and 1. It is most preferable to construct such articles such that ζ is between about 0.9 and 1. It should be kept in mind that use of the article can spread the microbe-inhibiting efficacy; therefore, the effective ζ of an article may increase with use from it as-manufactured value.

Combinations may be used to create preferred bedding articles for pets. A preferred case is to blend conventional fiber with fiber containing a diffusing microbe-inhibiting agent and use the blend to fill a containment structure whose outer surface has been treated with a strongly bonded microbe-inhibiting agent. Alternatively, one can also use the blend to fill a containment structure whose inner surface has been coated with a latex compound in which a microbe-inhibiting agent is incorporated (the agent in this coating will diffuse to some degree).

Generally, the denier of the fibers should preferably be between 0.8 and 20, and most preferably between 1 and 15. The cut length of the fiber should preferably be between 0.1 and 8 inches, most preferably between 0.4 and 5 inches.

Compaction Pre-Treatment of Fiber

As discussed earlier, when diffusing microbe-inhibiting agents are used, the diffusion of the agents from fibers which initially contained the microbe-inhibiting agents to fibers which did not is an important aspect of the resulting microbe-inhibiting efficacy of the article. The kinetics of this diffusion, in terms of distance that the microbe-inhibiting agents diffuse, are governed by an effective diffusion coefficient, D. To expose more fiber to the microbe-inhibiting agent in a given amount of time, one can maintain the fiber in a compacted state.

Markedly increased efficacy can thereby be obtained by maintaining the fiber in a compacted state for a period of time before using it as filling for microbe-inhibiting articles of the present invention. Homogenization of the microbe-inhibiting agent occurs at a greatly accelerated rate when the fibers are so compacted; and bedding articles fabricated from such fiber will possess a relative uniformity of microbe-inhibiting agent concentration that is needed for efficacy in the demanding environment in which the bedding articles are used.

The degrees of compaction should be such that the fiber is at a relative volume fraction of greater than 10%, preferably greater than 14%, and most preferably greater than 18%. Compaction should not be so strong that the fiber is damaged (e.g., compaction levels greater than about 40% may do more harm than good).

The desired compaction time is determined by the diffusivity of the microbe-inhibiting agent from the initially microbe-inhibiting fiber to the initially non-microbe-inhibiting fiber. One can perform diffusion calculations appropriate for a porous medium to determine the appropriate times.

The "relative volume fraction" of the fiber is defined as the fraction of a given volume that is occupied by the fiber material. One way to calculate this is as follows: Take the geometric volume occupied by the fiber (i.e., the volume the fiber appears to occupy); weigh the fiber in this volume; from the known fiber effective density, calculate the volume actually occupied by the fiber; divide this volume by the geometric volume to obtain the volume fraction occupied by the fiber. (If the fiber is of the "hollow" type, allowances must be made.)

Increasing the temperature will also increase the effective diffusion coefficient; and if this can be done cost effectively (which is often a problem) and at a temperature which is below any degradation temperature associated with the microbe-inhibiting agents, it can be a useful aid for homogenization.

Increasing local humidity can also raise the effective diffusion coefficient of many microbe-inhibiting agents (especially those agents which possess a good-moderate degree of water solubility).

Empirical Sample Uses of the Present Teaching

Consider a bedding article for a pet in which the inner tick has a containment volume of $V_c$=50,000 $cm^3$, and which is to be made using a combination of a diffusing agent microbe-inhibiting triacetate fiber and a conventional non-microbe-inhibiting polyester fiber. The triacetate fiber has a density, ρ, of about 1.32 gm/$cm^3$; and the polyester fiber has a density, ρ, of about 1.39 gm/$cm^3$. For a total blend density $\rho_B$=4%, and an average blend concentration of $C_B$=0.09%, the $\rho_B C_B$-product is 0.36 (in units of $\%^2$), which is close to the value corresponding to the $\rho_B C_B$=0.35 curve of FIG. 7. Suppose it is desired to use microbe-inhibiting fiber containing 0.3% of an agent similar to 2,4,4'-trichloro-2'-hydroxydiphenol. Using FIG. 7, this corresponds to an $x_o$-value of about 1.2%. This corresponds to a volume of 600 $cm^3$, or about 790 gm of the triacetate fiber. The remaining 2.8% (or 1400 $cm^3$) of the fill volume is to be occupied by polyester fiber. This corresponds to about 1.9 kg of the polyester fiber. Thus the appropriate blend contains 1.9 kg of polyester fiber and 790 gm of triacetate fiber inserted into the 50,000 $cm^3$ inner tick structure.

Zone-of-Inhibition Sample Uses of the Present Teaching

Consider a fiber-filled pet bed whose inner tick has a containment volume of $V_c$=60,000 $cm^3$, and which is to be made using a combination of a diffusing agent microbe-inhibiting acrylic fiber having an approximately circular cross-section and a conventional non-microbe-inhibiting polyester fiber. The acrylic fiber has a density, ρ, of about 1.18 gm/$cm^3$ and a denier of 3. The effective radial extent of the zone of inhibition of the fiber is measured to be about 70 Mm. The polyester fiber has a density, ρ, of about 1.39 gm/$cm^3$.

A 3 denier fiber with density 1.18 gm/$cm^3$ possesses an effective average radius of about 6.7 Mm. α for this system is therefore about 10.4. The behavior of this fiber will be close to that described by the "α=10" curve in FIG. 6. From the curve, it is seen that ρ approaches unity at $x_o$-values of about 4%–6% (0.04–0.06 in the figure). This corresponds to a volume of about 2400–3600 $cm^3$ or a mass of about 2.8–4.2 kg. Therefore, to ensure that most of the interior of the containment structure is within a zone of inhibition, it is necessary to include about 2.8–4.2 kg of the microbe-inhibiting acrylic fiber in the inner tick. Assuming it is desired to for the containment structure to have a total filled volume of 8%, one must include a volume fraction of the polyester blend of about 4%–2%. The corresponds to a volume of about 2400–1200 $cm^3$ or a mass of about 3.3–1.7 kg. The fibers should be well blended together.

Manufacture of Microbe-Inhibiting Bedding Articles for Pets

The manufacture of a pet bed begins with the conversion of textiles from roll to the appropriate size. The textiles may be based on a variety of natural or synthetic fibers, including cotton or polyester-cotton. The conversion is accomplished by die-cutting the roll into appropriately sized pieces or by spreading the fabric and cutting the pieces with an Eastman knife or the like. The cut pieces comprise a cover for the bed. Two cut halves, comprising a top and a bottom, are sewn together along the perimeter. As desired, a zipper or Velcro™ strip or buttons may be provided along a portion of the perimeter. Relative to bedding articles for humans, pet beds generally have a dimensional ratio which is closer to unity (pets beds are more square or circular rather than rectangular or oblong).

Microbe-Inhibiting Fillings

Microbe-inhibiting properties can be conferred to the bed by using a filling which is comprised of microbe-inhibiting material and/or by using a cover material which possesses microbe-inhibiting properties. If fiber is to be used as a filling, it is weighed, shredded, and blended (as through a shredder/picker) and stuffed (as by blowing using a blowing machine) into a containment structure (i.e., an inner "tick").

Another filling which may be used is comprised of a blend of conventional polyester non-microbe-inhibiting fiber and microbe-inhibiting particulate matter in which the microbe-inhibiting properties of the particulate are provided by incorporation of a diffusing microbe-inhibiting agent. The microbe-inhibiting particulate matter can be obtained in a variety of ways. For example, one can form polystyrene beads incorporated with Microban B anti-microbial agent.

One can also incorporate microbe-inhibiting agents into various zeolitic particulates. The zone of inhibition corresponding to the particulate is essentially three-dimensional in character. Relative to the fibrous (essentially two-dimensional) case, and to the extent that oc remains constant, a lesser volume fraction of the particles ($x_o$) is generally required for most of the containment material to be within a zone of inhibition. The relative composition should be such that the anti-microbial particulate comprises a volume fraction of the containment structure of more than about 1%, preferably more than about 3%, and most preferably more than about 5%. The remaining (non-microbe-inhibiting) fiber is added in an amount such that the fiber comprises between 0.1% and 15%; preferably between 0.6% and 10%; and most preferably between 1% and 8%.

Alternatively, shredded foam, polystyrene beads, or other non-fiber-based material may be substituted, in part or in whole, for conventional fiber and used in conjunction with antimicrobially-treated fiber.

Microbe-Inhibiting Linings

Another means of imparting microbe-inhibiting properties to the bedding article is to utilize a microbe-inhibiting liner, as shown generally as 18 in FIG. 4. The layer 18 may be adhered to the cover or filler to form a laminate (not shown), or may be a separate layer as shown in FIG. 4. This means may be used alone or in conjunction with the use of microbe-inhibiting filler and/or cover materials. For example, microbe-inhibiting flexible plastic sheets may be cut along with the cover material. These plastic sheets may then be placed on the backside (i.e., inner side) of the cut cover materials before sewing. The subsequent sewing process will thereby incorporate a microbe-inhibiting plastic layer on the inside of the cover. The cover may then be filled in the usual manner. Alternatively, the lining may be part of an outer cover material and/or an inner tick which contains filling material.

Plastic linings are effective both because they can be treated with microbe-cidal agents and because they can be obtained relatively impermeable to microbes, liquids, dirt, dust, excrement, etc. Even if the linings do not possess microbe-cidal properties, they can still possess significant microbe-inhibiting properties by virtue of their impermeability to microbes and to material that encourages the proliferation of microbes.

Microbe-inhibiting vinyl sheet is a preferred material for the lining. The material may comprise a microbe-cidal treated vinyl sheet or it may comprise a laminate structure with at least one layer comprising a microbe-cidal treated plastic sheet. A difficulty with this type of material is that it tends to be somewhat stiff; and the sewing process tends to require more dexterity and control—resulting in less efficient manufacturing. To ameliorate this difficulty, softer, more pliable plastics are preferred. These may be obtained, e.g., by using thin vinyl sheeting or by using increased concentrations of non-microbially-digestible plasticizer in manufacturing the plastic. Alternatively, one may bond the plastic sheet to the fabric. The bond may be weak (as via static electricity or a weak adhesive) or it may be strong (e.g., utilizing a coupling agent or an effective plastic-fabric adhesive).

One can use a microbe-inhibiting lining material as the sole material comprising the inner-tick. For example, a bag is constructed by die-cutting two plastic cut halves to a size a little smaller than outer containment structure. The appropriately shaped bag with an aperture may then be formed from the two plastic cut halves by placing one cut half on top of the other, sewing the perimeter (but leaving an aperture sufficient for filling), and then filling and sealing in the usual manner. This inner tick may then be placed inside the outer containment structure.

A preferred means for incorporating a lining without increasing the dexterity and control required to attach the lining to the containment material is to employ a microbe-inhibiting soft fabric rather than a microbe-inhibiting plastic sheet. Microbe-inhibiting cotton is a preferred material, as are polyester/cotton blends and acrylic-based fabrics. These fabrics are generally permeable to microbes, liquids, dirt, dust, excrement, etc., and hence do not possess the microbe-impenetrable characteristics of the plastic sheeting used.

Rather than using a separate lining material, one can apply a coating of microbe-inhibiting plastic to the backside of the fabric comprising the containment material. It is preferred to use a latex suspension to which a microbe-inhibiting agent has been added. The resulting suspension can be applied to the backside of the containment material using, e.g., a brush or a roller. The resulting latex coating provides microbe-cidal protection due to the incorporated microbe-cidal agent; microbe-impenetrable protection (if the coating is continuous across the fabric); and desirable physical characteristics such as increased dimensional stability, increased durability, and increased resilience. It can also facilitate cutting operations. Such latex coatings are particularly efficacious because they can be applied so that the resulting fabrics do not have an excessively stiff feel. Polyurethane coatings with added microbe-inhibiting agents are also preferred.

Non-Woven Articles

A desirable type of bedding article or insert to the outer containment structure of a bedding articles may be constructed from an extremely high-loft non-woven material structure, such as those used in filtration systems. The high-loft, low density material may be prepared by means know in the art (e.g., from extruded continuous filaments or from fiber webs or batts strengthened by bonding between or among fibers). The fiber bonding may be brought about by heating (including the use of low-melting coatings), by using adhesives, stitch-bonding, or mechanical interlocking (e.g., needling). The material may then be cut into the desired shapes. If the fibers comprising the non-woven structure are very well-bonded to each other, the cut structure may be used as-is as a bedding article. If they are not sufficiently well-bonded, one can seal the outer perimeter of the structure by some other means (e.g., local heating, stitching, serging, tacking, etc.). If the structure is to be used as the filling material inserted in a containment structure, then the degree of bonding is not very important.

Bedding articles for pets of this type using conventional fibers formed in layers is disclosed in U.S. Pat. No. 5,363,804 and U.S. Pat. No. 5,515,811.

These non-woven structures may be made microbe-inhibiting by use of microbe-inhibiting fibers or fiber blends, where the fibers are incorporated with a microbe-inhibiting agent at the time of their manufacture or post-treated with a microbe-inhibiting agent. If an agent of the diffusing type is used, only a fraction of the fibers is required to be initially microbe-inhibiting (the magnitude of this fraction is determined in the same manner as for the fiber-fill). If the agent is of the strongly bonded type, it is preferred that most (if not all) of the fiber be initially microbe-inhibiting.

It is important to ensure that procedures used commonly in non-woven manufacture (e.g., heat-bonding, application of adhesives, etc.) does not diminish the microbe-inhibiting efficacy of the finished product. For example, heat-bonding must be done at a temperature lower than the degradation temperature of the microbe-inhibiting agents used. Adhesives or low-melt outer coatings must not block the diffusion of microbe-inhibiting agents (in the diffusing agent case) or overcoat the microbe-inhibiting surface (in the strongly-bonded agent case).

In cases where the adhesive or other coatings only need to be applied to a fraction of the fibers or filaments and the microbe-inhibiting agents only need to be incorporated into a fraction of the fibers or filaments, it is preferred that these fractions be separate. It cases where this is not advisable (e.g., the fiber fraction which needs to be incorporated with a microbe-inhibiting agent is too large, or a strongly bonded agent is being used), it is preferred to post-treat the high-loft batting when it is in roll form (i.e., after it is already bonded), using a bath or spray technique. A particularly preferred non-woven material for the present invention is a very high-loft low density type such as those used in filtration systems. The materials may be purchased from a filter manufacturer in roll form and then post-treated or may be incorporated in the fibers which comprise the filter.

Odor-Control

Bedding articles for pets have a tendency to emit odors. There are numerous causes for such odors, many of which are related to microbes. It is therefore an additional benefit of bedding articles for pets which possess microbe-inhibiting properties that such articles will frequently display a reduced tendency to develop odors.

A wide variety of anti-odor (or deodorizing) compositions are known in the art. Odor masking, the intentional concealment of one odor by another odor, is perhaps the most common means for controlling odors. Odor masking on fabrics can be accomplished using various perfumes, colognes, etc. Relatively high levels of the masking agent are often required for adequate concealment of the odor.

Odor modification, where the odor is changed, as by chemical modification, can also been used; and it is frequently preferred over odor masking. The odor may be modified to become less offensive or may be diminished or neutralized.

In many cases it is preferred to use an odor-absorbing material rather than a masking or modification agent. Odor absorbing materials are often "broad spectrum" in nature, i.e., they are effective in neutralizing many different odor-causing agents. Common odor absorbing materials include activated charcoal and zeolites. These materials are typically used in a particulate form. They may be incorporated into the bedding article for a pet in a variety of ways, as directly into the materials comprising the article during their manufacture; or added to some component of the article during its manufacture; or adhered to some component(s) of the article.

A further advantage of microbe-inhibiting bedding articles for pets of the present invention is that, if it is desired to incorporate deodorizing, odor-modifying, or odor-masking materials, less such materials are needed than in a comparable article which did not possess microbe-inhibiting properties.

A preferred class of zeolites for use as odor absorbants are the intermediate silicate/aluminate zeolites. The intermediate zeolites may be characterized as having silica/alumina molar ratios of less than about 10. With regard to the present invention, intermediate zeolites are often preferred over "high" zeolites. The intermediate zeolites possess a higher affinity for amine-type odors; they are generally more efficient in odor absorption because they typically have larger surface areas; they are generally more moisture tolerant; and they retain more of their odor absorbing capacity in water than do "high" zeolites.

Carbonaceous materials which serve effectively as absorbents for organic molecules are often referred to as activated carbon or activated charcoal. Many of these materials are suitable for use in the present invention. They are available from commercial sources under such trade names as Calgon-Type CPG, Type PCB, Type SGL, Type Cal, and Type OL.

In support of the invention, the following experiments were conducted:

EXAMPLE NO. 1

A 80,000 $cm^3$ cover structure is to be filled with a fiber blend; and the total blend is to comprise 2.75% of the total containment volume. The average blend concentration of the microbe-inhibiting agent is 0.15%. A triacetate fiber (density=1.32 $gm/cm^3$) in which was incorporated 0.5% triclosan anti-microbial agent during its manufacture, as well as conventional polyester fiber (density=1.39 $gm/cm^3$) are used.

The filling is prepared using the design equations in Section V of the Description. It is necessary to have the microbe-inhibiting triacetate fiber occupy a volume fraction of the containment structure equal to about 0.82%, and to have the conventional polyester fiber occupy a volume fraction of the containment structure equal to about 1.92%. 871 gm of the microbe-inhibiting triacetate fiber (with a denier of 6 and cut to a length of about 2") was therefore blended with 2.14 kg of conventional polyester fiber (with a denier of 6 and cut to a length of about 2").

EXAMPLE NO. 2

A 0.12 $m^3$ cover structure is to be filled with a fiber blend; and the total blend is to comprise 1.2% of the total containment volume. The average blend concentration of the microbe-inhibiting agent is to be greater than 0.29%. An acrylic fiber (density=1.18 $gm/cm^3$) in which was incorporated 0.65% triclosan anti-microbial agent during its manufacture, as well as conventional nylon fiber (density=1.14 $gm/cm^3$) are used.

Using the design equations in Section V of the Description, it is necessary to have the microbe-inhibiting acrylic fiber occupy a volume fraction of the containment structure equal to about 0.54%, and to have the conventional nylon fiber occupy a volume fraction equal to about 0.66%. 765 gm of the microbe-inhibiting acrylic triacetate fiber (with a denier of 3.5 and cut to a length of about 1.5") was therefore blended with 903 gm of conventional nylon fiber (with a denier of 5.5 and cut to a length of about 1.5"). In this case, the average blend concentration, $C_B$, is about 0.293%.

EXAMPLE NO. 3

A 50,000 $cm^3$ cover structure is to be filled with a fiber blend; and the total blend is to comprise 1.8% of the total containment volume. The average blend concentration of the microbe-inhibiting agent is to be 0.12%. A polypropylene fiber (density=0.93 $gm/cm^3$) in which was incorporated 0.2% Tri-n-butyltin maleate (Ultra Fresh DM-50) anti-microbial agent during its manufacture, as well as regular polyester fiber (density=1.39 $gm/cm^3$) are used.

Using the design equations in Section V of the Description, it is necessary to have the microbe-inhibiting polypropylene fiber occupy a volume fraction of the containment structure equal to about 1.08%, and to have the conventional polyester fiber occupy a volume fraction equal to about 0.72%. 502 gm of the microbe-inhibiting fiber (with a denier of 4 and cut to a length of about 2") was therefore blended with 500 gm of conventional polyester (with a denier of 5 and cut to a length of about 1.5").

EXAMPLE NO. 4

The present example comprises the manufacture of a rectangular bed for a dog. The bed possesses a fleece top, a poly-cotton print bottom, and a zipper (on the short side). The top material is comprised of synthetic lambswool, also known as fleece. This material has two sides: a fleece side, which simulates the fleece of a lamb; and a backing or back-side. The synthetic lambswool used has a weight of 17.5 oz/linear yard and is obtained on 60"-wide rolls.

A roll of the synthetic lambswool is laid out flat across a spreading table such that the fleece side is facing the table, and the back-side is marked to indicate the area to be cut (27"×36" rectangles, in this case). The synthetic lambswool is then cut using an Eastman rolling knife. The poly-cotton print material used for the bottom has a weight of 8 oz./linear yard and is obtained on 60"-wide rolls. A roll of the poly-cotton print material is laid out flat across a spreading table such that the print side is facing the table. The back-side is marked to indicate the area to be cut (27"×36" rectangles). The poly-cotton print material is then cut using an Eastman rolling knife.

The cut halves (comprising the synthetic lambswool top and the poly-cotton bottom) are placed together such that the fleece-side of the synthetic lambswool is facing the print-side of the poly-cotton material, and the two cut halves are sewn together along their mutual perimeter, excluding one of the 27" sides. The sewn material is then flipped inside-out such that the fleece side of the synthetic lambswool and the print side of the poly-cotton material are on the exterior of the sewn material, and the sewing is at the interior. A 27" No. 3 nylon zipper is then sewn into the unsewn 27" side such that access to the interior may be obtained by opening the zipper. The resulting structure is referred to as a "cover."

An "inner tick," which is a bag or containment structure for holding the microbe-inhibiting fiber blend, is constructed in a manner similar to that of the cover. Two sheets of non-woven polypropylene are cut into 27"×36" rectangles (cut halves). The cut halves are then sewn together along their perimeter, excluding one of the 27" sides.

The interior of the inner tick has a volume of about 72,000 cm". The tick is filled with an acrylic fiber blend to a volume density of about 1.1%; and the average blend concentration is 0.08%. The fibers had been solution-spun, with triclosan added to the spin dope to produce fibers containing about 0.5% triclosan. The fiber is cut to a length of 1", and is blended with conventional acrylic fiber, which had also been solution-spun, cut to a length of about 1". Both fibers have a denier of 3.5.

Using the design guidelines of Section V, 374 gm of the microbe-inhibiting acrylic fiber is blended with 561 gm of the regular acrylic fiber; and the blend is inserted into the inner tick, which is then sewn shut.

The inner tick is placed inside the cover structure, and the zipper is closed. The microbe-inhibiting pet bed is then ready for packaging.

EXAMPLE NO. 5

An outer cover structure containing a zipper closure is fabricated as in Example No. 4 (using the same dimensions and materials). The inner tick of the pet bed is provided with microbe-inhibiting properties by using a sheet material which was provided with microbe-inhibiting properties at its time of manufacture. The unfilled inner tick is constructed in the same manner as was the conventional inner tick in Specific Example No. 4. (same dimensions), except white Staph-Chek Microvent Comfort fabric (Herculite Products, Inc.) is used in place of the non-woven polypropylene. The microbe-inhibiting inner tick is then filled with filled with 1.1 kg of conventional polyester fiber, and sewn closed. The inner tick is then inserted into the outer cover structure, and the zipper is closed.

EXAMPLE NO. 6

A microbe inhibiting outer cover material is constructed as follows. Synthetic lambswool and the poly-cotton print material are sized and cut in the same manner and to the same dimensions as in Example No. 4. Two sheets of white Staph-Chek Microvent Comfort fabric (Herculite Products, Inc.) are cut to the same dimensions as the lambswool and the poly-cotton print material. The synthetic lambswool top and the poly-cotton bottom are placed together such that the fleece-side of the synthetic lambswool is facing the print-side of the poly-cotton material. The two plastic sheets are then placed directly in contact with the backsides of the latter two materials. The four-layer composite is then sewn as was the two-layer composite in Example No. 4 and the zipper is similarly attached. An inner tick containment structure is constructed using the same dimensions and materials as in Example No. 4. In this example, however, the inner tick is filled with a blend of 500 gm of conventional polyester fiber and 500 gm of conventional polypropylene fiber. The inner tick is sewn closed and then inserted into the outer cover structure, and the latter is zippered shut.

EXAMPLE NO. 7

The cover material of the pet bed is here provided with microbe-inhibiting properties by use of a topical treatment. The treatment is carried out before the shapes are cut. Rolls of the synthetic lambswool and of the poly-cotton materials are unrolled and taken up onto initially-empty rolls. While the fabrics are in the unrolled state between the two rolls, they are sprayed with a microbe-cidal solution and dried. The solution is obtained by mixing 5 oz. of Quat EPA 12 with 1 gallon of purified water. (The active ingredient of Quat EPA 12 is the quaternary ammonium compound, alkyl dimethyl benzyl ammonium chloride.)

The treated fabrics are cut and used to form a zippered cover for a pet bed as in Example No. 4. An inner tick containment structure is manufactured using the same dimensions materials as in Example IV. The filling of the inner tick, however, is composed fully of conventional polyester fiber, of which 1.3 kg is blown into the inner tick. The inner tick is then inserted into the cover; and the zipper is closed.

EXAMPLE NO. 8

The pet bed is hereby provided with microbe-inhibiting properties by incorporating both a microbe-cidal liner and microbe-cidal fill. The bed is constructed in the same manner, using the same materials and dimensions as in Example No. 4, except that in the present example, the inner tick is fabricated using from two sheets of white Staph-Chek Microvent Soft fabric (Herculite Products, Inc.).

EXAMPLE NO. 9

The pet bed is hereby provided with microbe-inhibiting properties by incorporating both a microbe-cidal liner and microbe-cidal fill. The bed is constructed in the same manner, using the same materials and dimensions as in Example No. 4 except that in the present example, the inner tick is fabricated using from two sheets of Aegis High Density (tight-weave antibacterial fabric available from Precision Fabrics Group, Inc.)

EXAMPLE NO. 10

A microbe-inhibiting fleece rug for a pet to rest upon is manufactured as follows: A high-pile fleece fabric is prepared in which the polyester fibers (which comprise nearly all of the fleece) are incorporated with triclosan at the time of manufacture of the fibers. The concentration of the triclosan is 0.08%. The material is cut with a knife to a size of 20" by 40".

EXAMPLE NO. 11

A large piece of Polyfill Extra-Loft Antibacterial Batting (a non-woven polyester treated with Dow Corning 5700 anti-microbial agent, available from Fairfield Processing Corporation) is spread out on a cutting table. 5 pieces of the material are cut with a knife to a size of 22"×30". All 5 pieces are placed together, one on top of the other. They are serged together along the mutual perimeter. An outer cover structure with a zipper is made using the same materials and dimensions as in Example No. 4. The composite high-loft non-woven material is then inserted into the outer cover structure, and the zipper is closed.

EXAMPLE NO. 12

A 2"-high polyurethane foam (volume density about 1.2%) is fabricated with about 0.08% Tri-n-butyltin maleate (as Ultra Fresh DM-50). This material is cut with a knife to a size of 22"×30". An outer cover structure with a zipper is made as in Example IV. The foam material is then inserted into the outer cover structure, and the zipper is closed.

EXAMPLE NO. 13

An "egg-crate" therapeutic-type polyurethane foam (volume density about 1.8%) is fabricated with about 0.08% Tri-n-butyltin maleate (as Ultra Fresh DM-50). The peak height of the foam is about 1.75"; and the minimum height is about 0.5". This material is cut with a knife to a size of 22"×30". An outer cover structure with a zipper is made as in Example IV. The foam material is then inserted into the outer cover structure, and the zipper is closed. The resulting microbe-inhibiting bedding article for a pet is thus also provided with "therapeutic" qualities.

EXAMPLE NO. 14

An outer cover structure is made as in Example No. 4, except no zipper is attached. A 1"-high polyurethane foam (volume density about 2%) is fabricated with about 0.1% triclosan added to the precursor material. This foam is then die-cut into small (1"×1"×1") cubes. About two thousand of these cubes are inserted into the cover structure; and the aperture is then sewn closed.

EXAMPLE NO. 15

An outer cover structure with a zipper is made with the same dimensions and using the same sheepskin material as the top as in Example No. 4. For the bottom, however, A piece of Staph-Chek Synergy fabric (Herculite Products, Inc.), cut to a size of 27"×36", is used. 4 kg of an inner tick is fabricated to the same dimensions as in Example No. 4, but using two sheets of white Staph-Chek Microvent Soft fabric (Herculite Products, Inc.). The inner tick is filled with a blend of 500 g of Microsafe Acetate fiber (available from Celanese Acetate) and 4 kg of Poly-Pellets (polypropylene beads, available from Fairfield Processing Corporation), and sewn closed. The closed inner tick is inserted into the outer cover structure, which is then zippered shut.

What is claimed is:

1. A textile-based bedding article for a domestic animal comprising:
   an outer textile casing made from a tough, chew resistant material and which defines a geometric shape in the form of an article of a size which is adapted to support a domestic animal;
   a dry inner filling forming a mattress for the animal and encapsulated by the outer textile casing; and
   at least one of the outer textile casing and the inner filling having an effective microbe-inhibiting agent or property, wherein the microbe-inhibiting agent or property is non-toxic and non-carcinogenic when ingested by domestic animals at the levels used in the bedding article and further is non-skin-sensitizing on the skin or other membranes of the domestic animals who effectively come into contact with the bedding article.

2. A textile-based bedding article according to claim 1 wherein the outer textile casing is made from fiber selected from the group consisting of acrylics, polyester, nylon, olefin polymers, triacetate polymers, rubber, denim, vinyl and spandex.

3. A textile-based bedding article according to claim 2 wherein a compound is applied to or incorporated within the outer textile fabric to impart at least one of low surface energy, non-hydrophilic properties, antistatic properties, and antiadhesion properties.

4. A textile-based bedding article according to claim 2 wherein the outer textile casing comprises an outer fabric layer and the microbe-inhibiting agent or property comprises a laminate on an inner surface of the outer fabric layer.

5. A textile-based bedding article according to claim 4 wherein the microbe-inhibiting agent or property is selected from at least one of microbe-cidal, microbe-starving, and microbe-impenetrable agents.

6. A textile-based bedding article according to claim 4 wherein the laminate is a microbe-cidal laminate comprising a microbe-cidal agent selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, poly-substituted immine salts and phosphate esters, and mixtures thereof comprising a thermoplastic film or latex polymer.

7. A textile-based bedding article according to claim 4 wherein the laminate is a microbe-impenetrable laminate comprising a thermoplastic film or latex polymer.

8. A textile-based bedding article according to claim 7 wherein the thermoplastic film or latex polymer have applied thereto or incorporated therein a microbe-cidal agent.

9. A textile-based bedding article according to claim 2 wherein the inner filling comprises at least one of a foam, a particulate, and a fibrous filling.

10. A textile-based bedding article according to claim 9 wherein the inner filling comprises a non-woven fibrous filling selected from the group consisting of polyolefin, acrylic, nylon, polyester, polyurethane, polyethylene terephthalate, cellulose acetate, triacetate resin fibers and blends thereof.

11. A textile-based bedding article according to claim 10 wherein the fibrous filling is a blend of fibers, only a portion of which have a microbe-cidal agent applied thereto or incorporated therein.

12. A textile-based bedding article according to claim 11 wherein between 0.3 and 4.5 percent of a total amount of combined fibrous filling and outer textile casing fiber have said microbe-inhibiting agent incorporated therein.

13. A textile-based bedding article according to claim 12 wherein said bedding article further comprises at least one odor controlling agent, selected from at least one of an odor masking, an odor modifying, and an odor absorbing agent, included in at least one of said outer textile casing and said inner filling.

14. A textile-based bedding article according to claim 1 wherein the outer textile casing comprises an outer fabric and an inner layer of a flexible film having the microbe-cidal agent applied thereto or incorporated therein.

15. A textile-based bedding article according to claim 14 wherein the inner layer comprises a latex material which is coated onto the inner surface of the outer fabric layer.

16. A textile-based bedding article according to claim 1 wherein the microbe-inhibiting agent or property comprises a microbe-cidal agent selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, poly-substituted immine salts and phosphate esters, and mixtures thereof.

17. A textile-based bedding article according to claim 16 wherein the microbe-cidal inhibiting agent is chlorine dioxide.

18. A textile-based bedding article according to claim 16 wherein the microbe-cidal agent is 2,4,4'-trichloro-2'-hydroxydiphenol.

19. A textile-based bedding article according to claim 18 wherein the 2,4,4'-trichloro-2'-hydroxydiphenol is applied to or incorporated into at least a portion of the fibers in at least one of the textile casing and the inner filling.

20. A textile-based bedding article according to claim 19 wherein at least one of the outer textile casing and inner filling comprise acrylic fibers having 2,4,4'-trichloro-2'-hydroxydiphenol incorporated therein or applied thereto.

21. A textile-based bedding article according to claim 1 wherein the outer textile easing comprises a high pile component attached to a backing material to, in turn, form an artificial fleece.

22. A textile-based bedding article according to claim 1 wherein the microbe-inhibiting agent or property is selected from at least one of microbe-cidal, microbe-starving, and microbe-impenetrable agents.

23. A textile-based bedding article according to claim 1 wherein the inner filling comprises a fibrous filling selected from the group consisting of polyolefin, acrylic, nylon, polyester, polyurethane, polyethylene terephthalate, cellulose acetate, triacetate resin fibers and blends thereof; and wherein the microbe-inhibiting agent or property comprises a microbe-cidal compound which is less than fully bonded to at least a portion of the fibers in the filling and migrates to form a zone of inhibition.

24. A textile-based bedding article according to claim 23 wherein the microbe-inhibiting agent or property is also present in the outer casing.

25. A textile-based bedding article according to claim 24 wherein the microbe-inhibiting agent or property comprises a compound selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, poly-substituted immine salts and phosphate esters, and mixtures thereof.

26. A textile-based bedding article according to claim 1 and further comprising an odor-absorbing agent, selected from at least one of an activated carbon and a zeolite compound, included in at least one of said outer textile casing and said inner filling.

27. A textile-based bedding article according to claim 1 wherein at least one of the outer casing and the inner filling is impregnated with a flame resistant modacrylic polymer.

28. A textile-based bedding article according to claim 10 wherein the microbe-inhibiting agent or property comprises a microbe-cidal agent selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, poly-substituted immine salts and phosphate esters, and mixtures thereof.

29. A textile-based bedding article according to claim 28 wherein the microbe-cidal agent is chlorine dioxide.

30. A textile-based bedding article according to claim 28 wherein the microbe-cidal agent is 2,4,4'-trichloro-2'-hydroxydiphenol.

31. A textile-based bedding article according to claim 30 wherein the 2,4,4'-trichloro-2'-hydroxydiphenol is applied to or incorporated into at least a portion of the fibers in at least one of the textile casing and the fibrous filling.

32. A textile-based bedding article according to claim 31 wherein 2,4,4'-trichloro-2'-hydroxydiphenol is applied to or incorporated into acrylic fibers.

33. A textile-based bedding article according to claim 28 wherein the microbe-cidal agent is applied to or incorporated within the fibers in at least one of the outer textile casing and the inner filling.

34. A textile-based bedding article according to claim 28 wherein the microbe-cidal agent is present from 0.001 to 10 percent by weight of the fibers in the fibrous filling.

35. A textile-based bedding article according to claim 28 wherein the microbe-cidal agent is water-insoluble.

36. A textile-based bedding article according to claim 28, wherein the microbe-cidal agent retains microbe-cidal activity and remains a part of said bedding article following contact with pet bodily fluids and repeated laundering of said bedding article.

37. A bedding article for a domestic animal comprising:
  an air-permeable, unitary piece of non-woven material defining a geometric shape in the form of an article of a size which is adapted to support a domestic animal and form a mattress for the animal; and
  a microbe-inhibiting agent applied to or incorporated directly within at least a portion of said unitary piece of material, wherein the microbe-inhibiting agent is non-toxic and non-carcinogenic when ingested by domestic animals at the levels used in the bedding article and further are non-skin-sensitizing on the skin or other membranes of the domestic animals who effectively come into contact with the bedding article.

38. A bedding article according to claim 37 wherein the microbe-inhibiting agent is selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, poly-substituted immine salts and phosphate esters, and mixtures thereof.

39. A bedding article according to claim 38 wherein the microbe-inhibiting agent is present from 0.05 to 10 percent by weight of the unitary piece of material.

40. A bedding article according to claim 38 wherein the microbe-inhibiting agent is 3-trimethoxysilylpropylmethyloctadecyl ammonium chloride.

41. A bedding article according to claim 38 wherein the microbe-inhibiting agent is 2,4,4'-trichloro-2'-hydroxydiphenol.

42. A bedding article according to claim 37 wherein the non-woven material comprises a fibrous filling selected from the group consisting of polyolefin, acrylic polymers, nylon, polyester, polyurethane, polyethylene terephthalate, cellulose acetate, triacetate resin fibers and blends thereof.

43. A bedding article according to claim 42 wherein the fibrous filling comprises acrylic polymers from a group comprising acrylonitrile, vinyl acetate, methacrylate, methyl methacrylate and blends thereof.

44. A bedding article according to claim 37, wherein said microbe-inhibiting agent is water-insoluble.

45. A process for imparting microbe-inhibiting properties to a pet bed having an outer textile casing formed of a touch, chew-resistant material and defining a geometric shape in the form of an article of a size which is adapted to support a domestic animal and having a dry inner filling of at least one of a foam, a particulate, and a fibrous filling, comprising the step of:
  applying or incorporating a microbe-inhibiting agent to at least one of the outer textile casing and the filling, wherein the microbe-inhibiting agent is non-toxic and non-carcinogenic when ingested by domestic animals at the levels used in the pet bed and further are non-skin-sensitizing on the skin or other membranes of the domestic animals who effectively come into contact with the pet bed,
  whereby proliferation of microbes is inhibited in an area that contacts a pet that rests on said pet bed.

46. A process according to claim 45 wherein the microbe-inhibiting agent comprises a microbe-cidal agent selected from at least one of the group consisting of heavy metal salts, halogenated dioxides, quaternary ammonium compounds, halogenated compounds, sulfur compounds, phenyl derivatives, phenoxy derivatives, thiazoles, chlorinated phenolic compounds, poly-substituted immine salts and phosphate esters, and mixtures thereof.

47. A process according to claim 46 wherein the microbe-cidal agent is chlorine dioxide.

48. A process according to claim 46 wherein the microbe-cidal agent is 2,4,4'-trichloro-2'-hydroxydiphenol.

49. A process according to claim 46 wherein the fibrous filling is selected from the group consisting of polyolefin, acrylic, nylon, polyester, polyurethane, polyethylene terephthalate, cellulose acetate, triacetate resin fibers and blends thereof.

50. A process according to claim 49 and further comprising the step of applying or incorporating the microbe-cidal agent to only a portion of the fibers in the fibrous filling and then encasing the fibrous filling with the outer textile casing.

51. A process according to claim 50 and further comprising the step of melt spinning the portion of fibers and the applying or incorporating step comprises adding the microbe-cidal agent into the portion of the fibers during the melt spinning step.

52. A process according to claim 50 and further comprising the step of compacting the fibrous fillings, between the applying or incorporating and a step of encasing the fibrous filling with the outer textile casing, for a time and at a temperature sufficient to diffuse at least a portion of the microbe-cidal agent from the portion of the fibrous filling with the microbe-cidal agent to a second portion of the fibrous filling without the microbe-cidal agent.

53. A process according to claim 52 wherein the compacting step comprises compacting the fibrous filling so that a fraction of a volume, defined by said outer casing, that is occupied by the fibrous filling is at least 10 percent but no greater than 40 percent.

54. A process according to claim 53 wherein the fibrous filling is compacted so that said fraction is at least 14 percent.

55. A process according to claim 45 wherein the outer casing is a fabric selected from acrylics, polyester, nylon, olefin polymers, triacetate, rubber and spandex fibers.

56. A process according to claim 45, wherein said microbe-inhibiting agent is water-insoluble.

57. A process according to claim 45, wherein said microbe-inhibiting agent retains microbe-inhibiting activity and remains a part of said bedding article following contact with pet bodily fluids and repeated laundering of said bedding article.

\* \* \* \* \*